(12) United States Patent
Williams et al.

(10) Patent No.: US 6,734,024 B2
(45) Date of Patent: May 11, 2004

(54) FERROCENYL BORONATE DERIVATIZATION OF CHEMICAL COMPOUNDS UNDERGOING MASS SPECTROMETRY ANALYSIS

(75) Inventors: John Dudley Williams, Auburn, CA (US); Mary K. Young, Riverside, CA (US)

(73) Assignee: City of Hope, Duarte, CA (US)

( * ) Notice: Subject to any disclaimer, the term of this patent is extended or adjusted under 35 U.S.C. 154(b) by 235 days.

(21) Appl. No.: 09/921,988

(22) Filed: Aug. 6, 2001

(65) Prior Publication Data

US 2002/0019057 A1 Feb. 14, 2002

Related U.S. Application Data

(60) Provisional application No. 60/223,035, filed on Aug. 4, 2000.

(51) Int. Cl.$^7$ ............................................... G01N 24/00
(52) U.S. Cl. ............................. 436/173; 436/94; 436/95
(58) Field of Search .................................. 436/174, 173, 436/94, 95

(56) References Cited

PUBLICATIONS

Berkel et al. Derivatization for electrospray ionization mass spectrometry. 3. Electrochemically ionizable derivatives, Analytica Chemistry (1998), 70(8), 1544–1554.*

Yang et al. "Stereochemical effects in mass spectrometry (VII). Negative ion fast atom bombardment mass spectrometry of saccharides with areneboronic acids as reagents", Chemical Research in Chinese Universities (1992), 8(3), 23.*

Yang et al. "Reaction mass spectrometry of saccharides using areneboronic acids as reagents", Journal of Carbohydrate Chemistry (1993), 12(1), 39–48.*

Desaire et al. "Multicomponent quantification of diastereomeric hexosamine monosaccharides using ion trap tandem mass spectrometry", Anal. Chem.m 1999, vol. 71, pp. 1997–2002.*

Castro_Perez et al., "High–sensitivity LC–MS–MS for the automated identification of drug metabolites", http://www.iscpubs.com/articles/abl/b0004cas.pdf, Apr. 2000, pp. 38–44.*

Brooks et al. "Gas chromatography–mass spectrometry of cyclic boronate derivatives of some alkaloid and terpenoid diols", Heterocycles, vol. 28, No. 1, 1989, pp. 151–156.*

Takano et al. "A selected ion monitoring method for quantifying simvastatin and its acid form in human plasma, using the ferroceneboronate derivative" Biomed. Environm. Mass Spectrom., 1990, v. 19, pp. 577–581.*

Vaisir et al. "Cyclic boronates in the mass spectrometry of ecdysteroids", Rapid Comm. Mass Spectrom., 1993, v. 7, pp. 46–52.*

Young et al. "Analysis of N–acetylated hexosamine monosaccharides by ferrocenyl boronation and tandem electrospray ionization mass spectrometry", Rapid Commun. Mass Spectrom., 2000, v. 14, pp. 1462–1467.*

* cited by examiner

*Primary Examiner*—Yelena G. Gakh
(74) *Attorney, Agent, or Firm*—Rothwell, Figg, Ernst & Manbeck

(57) ABSTRACT

An improved mass spectrometry method comprises the analysis of ferrocenyl boronate derivatives of compounds of interest. Chemical derivatization with ferrocenyl boronate overcomes problems resolving small structural differences in a variety of biologically important compounds, including carbohydrates, ultimately increasing the propensity of an analyte to ionize and provide quality fragmentation during successive rounds of electrospray MS. The resultant full scan spectra reflect large amounts of structural information.

3 Claims, 33 Drawing Sheets

OTHER PUBLICATIONS

Gentili et al. "Analysis of free estrogenes and their conjugates in sewage and river waters by solid–phase extraction then liquid chromatography electrospray–tandem mass spectrometry", Chromatographia, 2002, v. 56, No. 1/2, pp. 25–32.*

Xu et al. "Stable isotape dilution high–performance liquid chromatography–electrospray ionization mass spectrometry method fo endogenous 2– and 4–hydroxyestrones in human urine", J. Chromatogr. B, 2002, v. 780.*

Brooks et al., "Analytical separation and characterisation of 1,2– and 1.3–diols as their cyclic ferroceneboronate derivatives," J. of Chromatography 362:113–116, 1986.

Brooks et al., "Cyclic Ferroceneboronates as Derivatives for the Gas Chromatographic Separation and Characterisation of diols and Related Compounds," J. of Chromatography 399:207–221, 1987, The Netherlands.

Davis et al., "A Microscale Electrospray Interface for On–Line, Capillary Liquid Chromatography/Tandem Mass Spectrometry of Complex Peptide Mixtures," Anal. Chem. 67:4549–4556, 1995.

Gamoh et al., "Chromatographic and Mass–Spectrometric Studies of Cyclic 2–(N,N–Dimethylaminomethyl)ferroceneboronates and Related Esters," Analytical Sciences 10:705–711, Oct. 1994.

Yoshimura et al., "$^{11}$B NMR studies on complexation of borate with linear and crosslinked polysaccharides," J. Chem. Soc., Faraday Trans., 92(4):651–656, 1996.

* cited by examiner

D-Glc Ferrocene Boronates Possible Routes of Fragmentation

Fragment Ions Derived from Sequential Carbon Loss

Fragment Ions Derived from Sequential Carbon Loss

Figure 11. Maltose Cellobiose & Lactose MS² Comparison

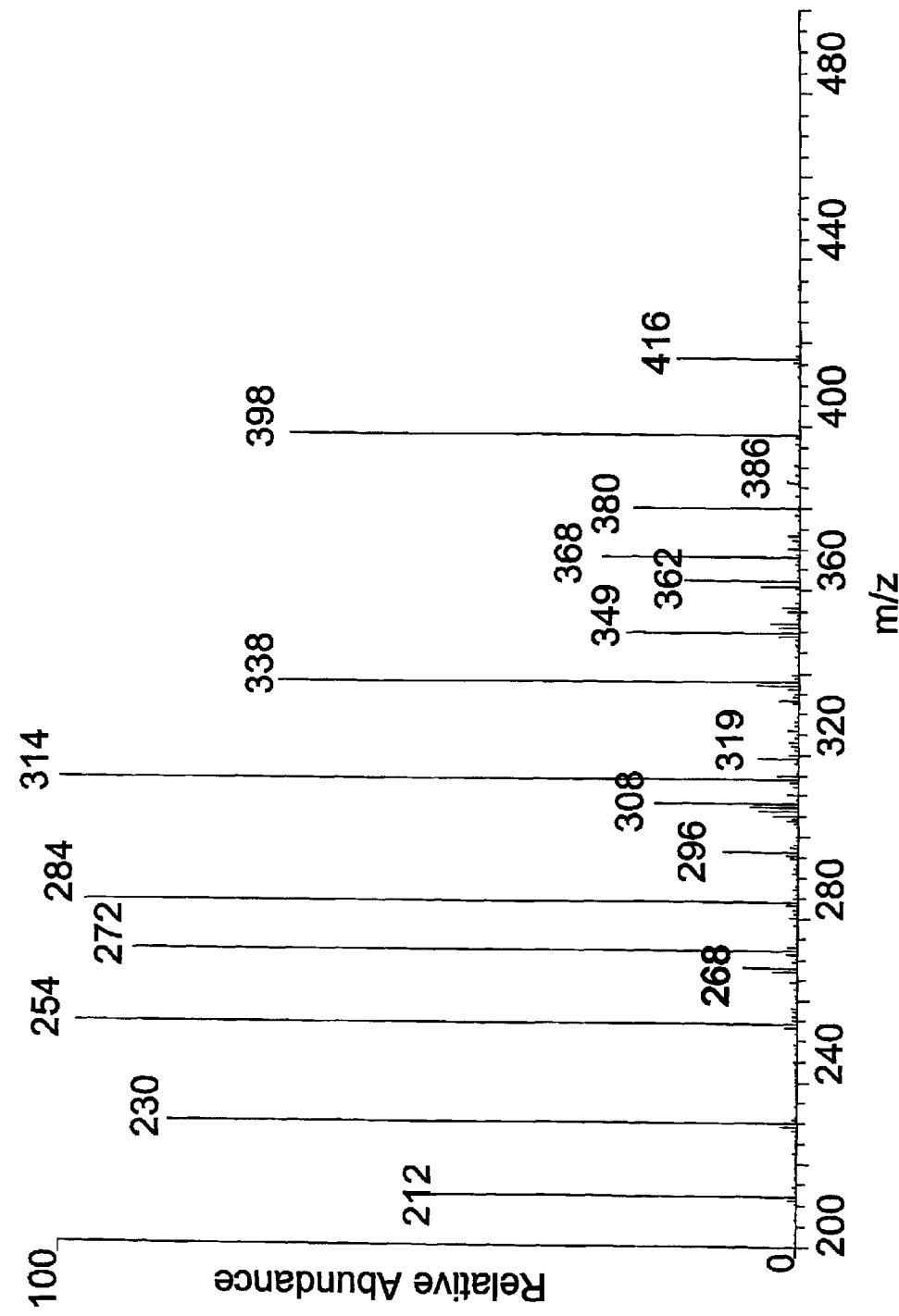
Figure 15f  C1=C13  GlcNAc

FERROCENYL BORONATE DERIVATIZATION OF CHEMICAL COMPOUNDS UNDERGOING MASS SPECTROMETRY ANALYSIS

CROSS-REFERENCES TO RELATED APPLICATIONS

A provisional application, No. 60/223,035, was filed Aug. 4, 2000.

FEDERALLY SPONSORED RESEARCH AND DEVELOPMENT

This invention was supported under Grant Nos. RR06217, ES08258 awarded by the National Medical Sciences, National Institutes of Health, Bethesda, Md. and the Cancer Center Core Grant CA33752. The United States Government maintains certain rights in the invention.

BACKGROUND OF THE INVENTION (1) Field of the Invention

This invention is directed generally to improvements to the analysis of chemical compounds using mass spectroscopy methods. More specifically, the invention relates to ferrocenyl boronate derivatization of chemical compounds to be analyzed and to their subsequent analysis using electrospray tandem mass spectrometry methods.

(2) Description of the Related Art

Mass spectroscopy is a well-known tool used for analyzing chemical compounds. Tandem mass spectroscopy, using electrospray ionization, has been used with increasing frequency for the analysis of biological samples. Persons skilled in analytical chemistry methods are familiar with the operation of electrospray tandem mass spectrometry instruments.

Currently a need exists for improved methodologies enabling one to chemically or mechanically manipulate large numbers of compounds in order to extract subtle differences in structure. A number of complex carbohydrates and esters are biologically significant molecules in that they contain a high degree of information per molecular unit and constitute a prevalent form of protein post-translational modification. (R. A. Dwek *Biochemical Society Transactions* 1995; 23: 1.) It is desirable not only to obtain amino acid sequences of a number of glycoproteins, but also to investigate the substance and microheterogeneity of certain portions of these molecules. (M. E. R. O'Brien, B. E. Souberbielle, M. E. Cowan, C. A. Allen, D. M. Luesley, J. J. Mould, G. R. P. Blackledge, G. R. B. Skinner *Cancer Letters* 1991; 58: 247.) Informational properties of chemical moieties are dependent on their high degree of conformational and isomeric diversity resulting from subtle changes in unit assembly. (R. A. Laine, *Glycobiology* 1994; 4: 749.) Changes in compound architecture often reflect major biological implications, including disease. (S. I. Hakormori *Cancer Research* 1985; 45: 2405; A. Eiras-Segal, M. V. Croce, *Allegol. Et. Immunopathol.* 1998; 25: 176; I. Brockhausen, *Biochemical Society Transactions* 1997; 25: 871; C. M. Martersteck, N. L. Kedersha, D. Drapp, T. Tsui, K. J. Colley, *Glycobiology* 1996; 6: 289; D. Naor, R. V. Sionov, D. Ish-Shalom, *Cancer Research* 1997; 71; 241; K. O. Lloyd, *Cancer Biology* 1991; 2: 421; S. Leppa, J. Heino; M. Jalkanen, *Cell Growth and Differentiation* 1995; 6: 853.) As a result, the number of potential biologically significant structures is significant. (B. Fernandes, U. Sagman, M. Auger, M. Demnetrio, J. W. Dennis, *Cancer Research* 1991; 51: 718.)

Structural elucidation of carbohydrates has been accomplished using a combination of techniques, usually nuclear magnetic resonance (NMR) and mass spectrometry (MS). These techniques have proven labor intensive. (J. F. Kennedy, G. Pagliuca, *Oligosaccharides*: Second Edition ed.; J. F. Kennedy, G. Pagliuca, Ed.; IRL Press at Oxford University Press: Oxford, New York, Tokyo, 1994, pp. 43–68).

Tandem MS, particularly electrospray quadruple ion-trap MS (ES-MS) is well suited for examining complex mixtures, particularly when coupled with a front-end separation system such as liquid chromatography (LC-MS). (N. Kawasaki,; M. Ohta; S. Hyuga; O. Hashimoto; T. Hayakawa. *Analytical Biochemistry* 1999, 269, 297–303; M. Kohler; J. Leary. *Analytical Chemistry* 1995, 67, 3501–3508; H. Kwon, J. Kim. *Journal of Liquid Chromatography* 1995, 18, 1437–1449). ES-MS offers the possibility of working efficiently and with lower amounts of sample without the possibility of thermal losses, which can often be a requirement for the study of biological structure and function relationships. (N. H. Packer, M. J. Harrison, *Electrophoresis* 1998; 19: 1872). Great potential exists for ES-MS methods eliciting fine structural and relevant details in larger chemical units. (N. Viseux, E. de Hoffmann, B. Domon, *Anal. Chem.* 1998; 70: 4951.)

Peptide sequencing by MS methods has rapidly developed into a mature science. (D. F. Hunt, J. E. Alexander, L. Ashley, P. A. McCormack, H. M. Martino, J. Shabanowitz, N. Sherman, M. A. Mosely, J. W. Jorgenson, K. B. Tomer, *Mass Spectromebric Methods for Protein and Peptide Sequence Analysis*; Academic Pres, Inc.: San Diego, Calif., 1991.) On the other hand, because of the large differences in fragmentation energies found in carbohydrates, the application of these types of methods in the analysis of carbohydrates has been limited. Also, due to the poor ionization in ES-MS of information-rich sugars released from their parent molecule by application of enzymatic deglycosylation, this severely affects sensitivity and consequently hinders detection.

Many analytical methods for analysis of compounds involve some form of derivatization to enhance sensitivity or fragment information in the mass spectrometer. The analysis of certain compounds has relied on derivatization chemistry to enhance the sensitivity of these important biological compounds as applied to their specific techniques. (R. A. Dwek, *Biochemical Society Transactions* 1995, 23 1–25; C. M. Starr, R. I. Masada, C. Hague, E. Skop, J. C. Klock, *J. Chromatogr A* 1996, 720, 295–321; M. F. Chaplin, Monosaccharides; Second Edition; M. R. Chaplin, Ed. IRL Press at Oxford University Press: Oxford, New York, Tokyo, 1994, pp 1–40.) Chemical derivatization has been employed to overcome the ionization quandry. (D. J. Harvey, *J. Am. Soc. Mass Spectrom.* 2000, 11, 900–915; J. J. Pitt, J. Gorman, *Analytical Biochemistry* 1997, 248, 63–75; D. Williams, T. D. Lee, N. Dinh, M. K. Young, *Rapid Commun. Mass Spectrom* 2000, 14, 1530–1537; S. Susuki, K. Kakehi, S. Honda, *Anal Chem* 1996, 68, 2073–2083.)

Almost all methods of MS analysis of compounds rely heavily on some form of derivatization not only to increase sensitivity, but also to augment volatility and the proclivity to form useful fragment ions. Derivatization must not only increase the propensity of the analyte to ionize, but also provide the desired quality of fragment information during successive rounds of ES-MS. Desirable fragments should provide both selective loss of chemical units and, within these fragments, cross pyranose ring fissions should reflect subtle stereochemical differences between individual molecular units. (H. Desaire, J. A. Leary, *Anal. Chem.* 1999, 71, 1997–2002; Z. Zhou, S. Ogden, J. A. Leary *J. Org. Chem.* 1990, 55, 5444–5446; S. P. Gaucher, J. A. Leary *Anatylical Chemistry* 1998, 70, 3009–3014.) Cross pyranose ring fragmentation releases neutral fragments. The parent ion then characterizes the linkage position between molecular units. As a result, profiling, sequence identity and linkage position information may be explored. Normally, the larger molecules or compounds, particularly those that contain nitrogen in the form of N-acetylated aminohexose residues, can be electrosprayed with or without permethylation. However, the $MS^2$ fragmentation information is often not particularly informative due to simple water loss. This technique works even less reliably with smaller molecules found during enzymatic digestion protocols. As the molecule becomes smaller and contains fewer chargeable atoms (usually nitrogen) and a diminished propensity for cationization, the efficiency of ES-MS analysis declines. Considerable attention has been paid to various methods of mono and oligosaccharide complexation with a variety of metal ions. (H. Desaire,; J. A. Leary, *Anal. Chem.* 1999; 71: 1997; S. Konig, J. A. Leary, *Journal of the American Society for Mass Spectrometry* 1998; 9: 1125; G. Smith, J. A. Leary *Journal of the American Society for Mass Spectrometry* 1996; 7: 953; Z. Zhou, S. Ogden, J. A. Leary, *J. Org. Chem.* 1990; 44: 5444; M. Kohler, J. A. Leary, *Analytical Chemistry* 1995; 67: 3501; G. F. Hofineister, Z. Zhou, J. A. Leary, *J. Am. Chem. Soc.* 1991; 113: 5964.)

Furthermore, in certain cancer studies, the catechol estrogens 2-hydroxyestradiol (2-OHE) and 4-hydroxyestradiol (4-OHE) are implicated as so-called good and bad estrogens in the biogenesis of malignant cells (S. H. Safe, *Interactions Between Hormones and Chemicals in Breast Cancer*, Ann. Rev. Pharmacol. Toxicol., 1998. 38: p. 121–158; E. L. Cavalieri, et al., *Molecular Origin of Cancer: Catechol Estrogen-3,4-Quinones as Endogenous Tumor Initiatiors* Proc. Natl. Acad. Sci. USA, 1997. 94: 10937–10942; D. E. Stack, *Molecular Characteristics of Cathechol Estrogen Quinones in Reactions with Deoxyrbonucleosides* Chem. Res. Toxicol., 1996 9: 851–859; L. Shen et al., *Bioreductive Activation of Catechol Estrogen-ortho-quinones: Aromatization of the B ring in 4-Hydroxyequilenin markedly Alters Quinoid Formation and Reactivity.* Carcinogenesis, 1997. 18(5): 1093–1101.) It has been demonstrated that these compounds can be formed by cytochrome P450 hydroxylation of estradiol (E. L. Cavalieri, et al.). Modulation of these products is controlled through the action of catechol-O-methyl transferases, which methylate the newly introduced phenolic hydroxyl group. The so-called good estrogen (2-OHE) is thought to perform important positive roles within the cell such as the suppression of osteoporosis and atherosclerosis because of its ability to inhibit leucotriene synthesis, (J. Alanko, et al., *Catechol Estrogens as Inhibitors of Leucotriene Synthesis.* Biochemical Pharmacology, 1998. 55: 101–104.) a potent stimulator of bone readsorption. On the other hand, 4-OHE is prone to easy oxidation aid if it avoids methylation, glucuronidiation, sulfation or other neutralizing processes it may become oxidized to the semiquinone. The semiquinone is redox reactive and has been shown to depurinate DNA and produce significantly increased numbers of mammary cancers in animal models (L. Shen et al.; N. T. Telang, *Estradiol Metabolism: A Endocrine Biomarker for Modulation of Human Mammary Carcinogenesis.* Environmental Health Perspectives, 1997. 105 (3): 559–564.) An analogous mechanism has been postulated for the development of prostate cancer (J. F. Dorgan, et al., *Relationships of Androgens and Estrogens to Prostate Cancer Risk Results from a Prospective Study in Finland.* Cancer Epidemiology, Biomarkers & Prevention, 1998 7: 1069–1074.)

To better understand the links between these two bio-effector molecules in the context of both breast and prostate cancer, sensitive methods of analysis for these compounds are essential. To date the most common form of chemical analysis for catechol estrogens has been gas chromatography using mass spectrometric detection (GC-MS) or radiometric (tritiur release). (Jordan, S. W., I. S. Krull, and S. B. J. Smith, *The Trace Analysis for Catechol Derivatives via Boronate Ester Formation and GC-Microwave Induced Plasma Emission Spectroscopic Detection (GC-MIP)*. Analytical Letters, 1982. 15(A14): p. 1131–1148; Sepkovic, D. W., et al, *Catechol Estrogen Production in Rat Microsomes after Treatment with Indole-3-Carbinol, Ascorbigen, or β-Napthoflavone: A Comparison of Stable Isotope Dilution Gas Chromatography-Mass Spectrometry and Radiometric Methods.* Steroids, 1994. 59: p. 318–323.). These methods, although sensitive, all possess certain drawbacks. Electrospray mass spectrometry (ES-MS) has proven to be a robust and sensitive method for the detection and quantitation of both large and small molecules. (Cole, R. B., ed. *Electrospray Ionization Mass Spectrometry. Fundamentals, Instrumentation, and Applications.* 1 ed. 1997, John Wiley: New York, Chichester, Weinheim, Brisbane, Singapore, Toronto. 577.) However, most analyses involve aqueous organic liquid mixtures containing analytes that have easily ionizable functionalities. The analysis of neutral lipophilic compounds such as 2- and 4-OHE requires the use of a suitably non-polar solvent and a methodology for creating a charged species.

The present invention provides a sensitive and semi-quantitative method for analyzing both hydroxyestradiol isomers. The methodology utilizes ferrocenyl boronic acid derivatives (Brooks, C. J. W. and W. J. Cole, *Analytical Separation and Characterization of 1,2 and 1,3 diols as their Cyclic Ferrocene Boronate Derivatives.* Journal of Chromatography, 1986. 362: p. 113–116; Brooks, C. J. W. and W. J. Cole, *Cyclic Ferroceneboronates as Derivatives for the Gas Chromatographic Separation and Characterisation of Diols and Related Compounds.* Journal of Chromatography, 1987. 399: p. 207–221; Van Berkel, G. J., et at, *Derivatization for Electrospray Ionizable Mass Spectrometry.* 3. *Electrochemically Ionizable Derivatives.* Anal Chem, 1998. 70: p. 1544–1554; Van Berkel, G. J., et al, *Derivatization for Electrospray Ionization Mass Spectrometry.* 3. *Electrochemically Ionizable Derivatives.* Anal Chem., 1998. 70: p. 1544–1554) that undergo single-electron oxidation when sprayed from an ES interface having a large surface area electrode (Van Berkel, G. J. and F. Zhou, *Characterization of an Electrospray Ion Source as a Controlled-Current Electrolytic Cell.* Anal Chem, 1995. 67: p. 2916–2923; Van Berkel, G. J. and F. Zhou, *Electrochemistry Combined On-Line with Electrospray Mass Spectrometry.* Anal Chem, 1995. 67: p. 3643–3649; Van Berkel, G. J., S. A. McLuckey, and G. L. Glish, *Preforming Ions in a Solution via Charge-Transfer Complexation for Analysis by Electrospray Ionization Mass Spectrometry.* Analytical Chemistry, 1991. 63(18): p. 2064–2068.) Fragmentation spectra of the radical cation molecular ions of the two isomers are sufficiently different that their relative ratios in a mixture can be determined.

SUMMARY OF THE INVENTION

In accordance with one aspect of the invention, there is provided a new and improved method for analyzing chemical species using mass spectrometry. One or more species to be analyzed are labeled (derivatized) with ferrocenyl boronate and the labeled compounds are introduced into a mass spectrometer instrument. In preferred embodiments, the mass spectrometer uses electrospray tandem technology.

Another aspect of the invention relates to an inventive spray needle that acts as a controlled current electrochemical cell for an electrospray tandem MS instrument. The needle produced fragment ion spectrum to aid in identifying and analyzing compounds for subtle changes in structure.

A variety of chemical compounds can be analyzed in accordance with the present invention, including N-acetylated hexose carbohydrates (such as 2-N-acetamido-D-glucosamine, 2-N-acetamido mannosamine, 2-N-acetamidogalactosamine and lactofucsylatraose). Alternatively, the chemical compound may be a neutral isomeric low molecular weight carbohydrate such as an aldohexose, 6-dideoxyaldohexose where the aldohexoses and 6-dideoxyaldohexosis are preferably D-glucose, D-mannose, D-galactose, L-fructose or L-rhamnose. The chemical compound may be a disaccharide such as maltose, cellobiose, lactose, D-Glc disaccharide or an O-methyl glycoside. Other examples include catechol estrogens including 2-hydroxyestradiol and 4-hydroxyestradiol.

BRIEF DESCRIPTION OF THE DRAWINGS

Several embodiments of the invention are illustrated and described in the accompanying drawings, forming a part of the specification, wherein.

DETAILED DESCRIPTION OF PREFERRED EMBODIMENTS

Figure 1:
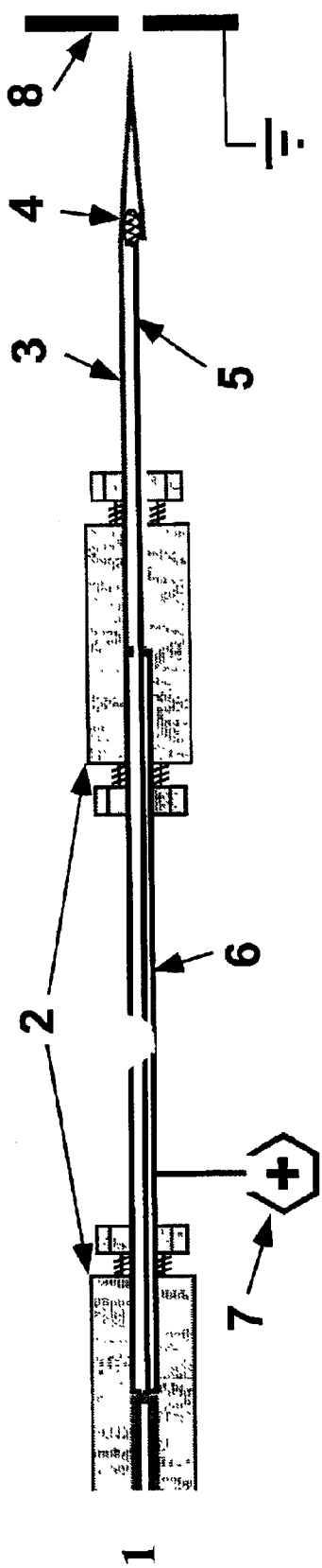
FIG. 1 is a schematic diagram showing an electrochemical cell which may be used to produce single electron oxidation of ferrocene-containing analytes.

The present invention provides improvements to the analysis of chemical compounds using MS technology. Specifically, the present invention permits the resolution of subtle distinctions among compounds which in the past were unresolvable or difficult to resolve. This is accomplished by forming ferrocene boronate derivatives of the compounds, and then analyzing the derivatized compounds using MS technology, preferably electrospray tandem MS technology. The derivatized compounds provide easily distinguishable patterns upon analysis.

The derivatizing reagent, ferrocene boronic acid (C. J. W. Brooks, W. J. Cole, *Journal of Chromatography* 1986; 362: 113; C. J. W. Brooks, K. W. Cole, *Journal of Chromatography* 1987; 399: 207) forms redox active cyclic five and six member rings with carbohydrates (K. Yoshimura, Y. Miyazaki, S. Sawada, H. Waki *J. Chem. Soc., Faraday Trans.* 1996; 92: 651). The resulting derivatives easily ionized by single electron loss (approx. 0.3–0.6 V). Previously, cyclic boronate esters have been utilized as protecting groups and the ferrocene boronates have been used to prepare stable products suitable for analysis by gas chromatography-mass spectrometry GC-MS [K. Gamoh, et al., *Chromatographic and Mass Spectrometric Studies of Cyclic 2-(N,N-Dimethylaminomethyl)ferrocenboronates and Related Cyclic Esters.* Analytical Sciences, 1994 10: 705–771]. Ferrocene boronate has a low redox potential (0.6 v vs. Ag/AgCl (J. A. Dean, Lange's Handbook of Chemistry, 14ed. 1992, New York: McGraw-Hill. 5.55) which allows it to be easily oxidized in preference to other organic species that generally have higher redox potentials. This is particularly true for aprotic organic solvents where the usual protonation reactions for the formation of electrospray ions are less favored. A supporting electrolyte is required in such solvents in order to provide sufficient current for the electrochemical reaction. Van Berkel and coworkers have shown that LiTrf functions well as a supporting electrolyte while keeping background ions at minimal levels (G. J. Van Berkel and F. Zhou, *Characterization of an Electrospray Ion Source as a Controlled-Current Electrolytic Cell.* Anal Chem., 1995. 67: 2916–2923).

Any electrospray source is intrinsically an electrochemical cell and the one electron oxidation of cyclic ferrocence boronate esters of suitable diols are readily observed using standard source designs. However, we have found that signal strength increased by as much as two orders of magnitude by increasing the surface area of the high voltage electrode in contact with the sample solution. In a preferred embodiment of the invention, ionization is carried out in an inventive electrochemical cell that doubles as a spray device.

The methods of the present invention are simple to perform and confer a variety of desirable characteristics including: 1) increased ability to ionize; 2) ion identification facilitated by production of a unique isotopic distribution; 3) production of informationally rich fragments (cross pyranose ring fragments); 4) modification of analyte solubility (less polar derivatives) and 5) generation of a molecular ion rather than a pseudo-molecular ion. Electro-spraying FcBor compounds through an electrochemical cell in positive ion mode produces a large signal increase (10–100 fold) when compared to normal spray modes due to the increased surface area of the electrode.

The present invention also provides an electrochemical cell, shown in FIG. 1, which is constructed from stainless steel (SS) and quartz tubing including a transfer line entry 1. The spray needle 3 is constructed from quartz 350/150 mm polyimide coated tubing (Polymicro Technologies, Phoenix, Ariz.) and is pulled into a fine needle using a laser-puller (Sutter Instruments Model 2000, Novato, Calif.). The spray-tip diameter is approximately 10 um. The interior of the spray needle is concentrically fitted with a 10 cm length of SS 100/50 mm tube. This tube extends to just behind the spray tip and is in contact with the spray tip frit. The frit 4 is constructed from Whatman GF/A glass fiber filter paper (Whatman, Clifton, N.J.) and is in internal electrical contact with the outer SS 8 cm tube 6, which forms the body of the cell. This SS tube is 350/150 mm (od/id) and is contained between two PEEK ZDV 2 tube junctions (Upchurch Scientific, Oakharbor, Wash.). The high voltage connector from the mass spectrometer is connected directly to the outer SS tube of the cell using an alligator clip 7. The internal SS tube 5 runs from the needle tip back along the entire length of the cell and serves to increase the surface area of the electrode. The MS heated capillary aperture is on the LCQ 8.

Using a normal electrospray apparatus, ferrocenyl derivatives may be oxidized owing to their low redox potential of around 0.3–0.6 V. However, by modifying the spray device in accordance with this aspect of the invention, using two sets of concentric SS tubes with the innermost tube terminating within a fritted quartz spray needle, considerable signal amplification is obtained. The actual increase over conventional spray devises has been shown to be about two orders of magnitude and is flow rate dependent. Optimal flow rates range between 50 and 2000 nL/min. The cell must first be tuned using the flow and voltage parameters to produce a maximal signal based on spraying a solution of $F_cBor$ of approximately 100 mM.

The invention is further illustrated by the following Examples, which are not meant to be limiting.

EXAMPLE 1

$F_cBor$, lithium triflate (LiTrf) and dimethyl sulfoxide (DMSO) were purchased from Aldrich Chemical Co. (Milwaukee, Wis.). The carbohydrate standards were obtained from Sigma Chemical Co. (St. Louis, Mo.). The solvents used, acetonitrile (MeCN) and dichloromethane (DCM) were purchased from Burdick and Jackson (Muskegon, Wis.). Pure water was obtained for preparing the mono and oligosaccharide standards (~1–3 mg/ml) from a Milli-Q (Millipore Inc.) water dispenser.

A Finnigan LCQ (Finnigan Instruments, Thermoquest Inc., San Jose, Calif.) ion-trap mass spectrometer was used to collect all MS data The LCQ's ion source was modified by removing the standard liquid flow head to expose the heated capillary (M. T. Davis; D. S. Stahl, S. A. Hefta, T. D. Lee. *Anal. Chem.* 1995; 67: 4549.) The instrument was then used to accept continuous direct flow injection from the electrochemical cell driven by the LCQ's built-in syringe pump. The cell was normally operated at 1–1.5 kV and a flow rate of 500 nl/min or less.

The aqueous stock solutions of the carbohydrate standards were used to produce diluted working solutions (final concentrations ~50–100 mM) by dilution 100:1 with working solution A. Working solution A was prepared from a mixture of MeCN/DCM, 90:10 v/v that contains a suitable working electrolyte, LiTrf. This reagent must be added to solutions being prepared for analysis using the electrochemical cell (ECC) at 100:1 dilution. The stock solution of LiTrf contains approximately 12 mg/ml of MECN. The final addition to the working solution A is the derivatizing agent $F_cBor$. The $F_cBor$ stock solution is made daily as required by dissolving 3–5 mg of $F_cBor$ in 1 ml of DMSO. A 100:1 dilution into 1 ml of working solution A is made during the derivatization reaction with the carbohydrates. The solution containing all components as described above is then sprayed immediately into the mass spectrometer.

Figure 2:
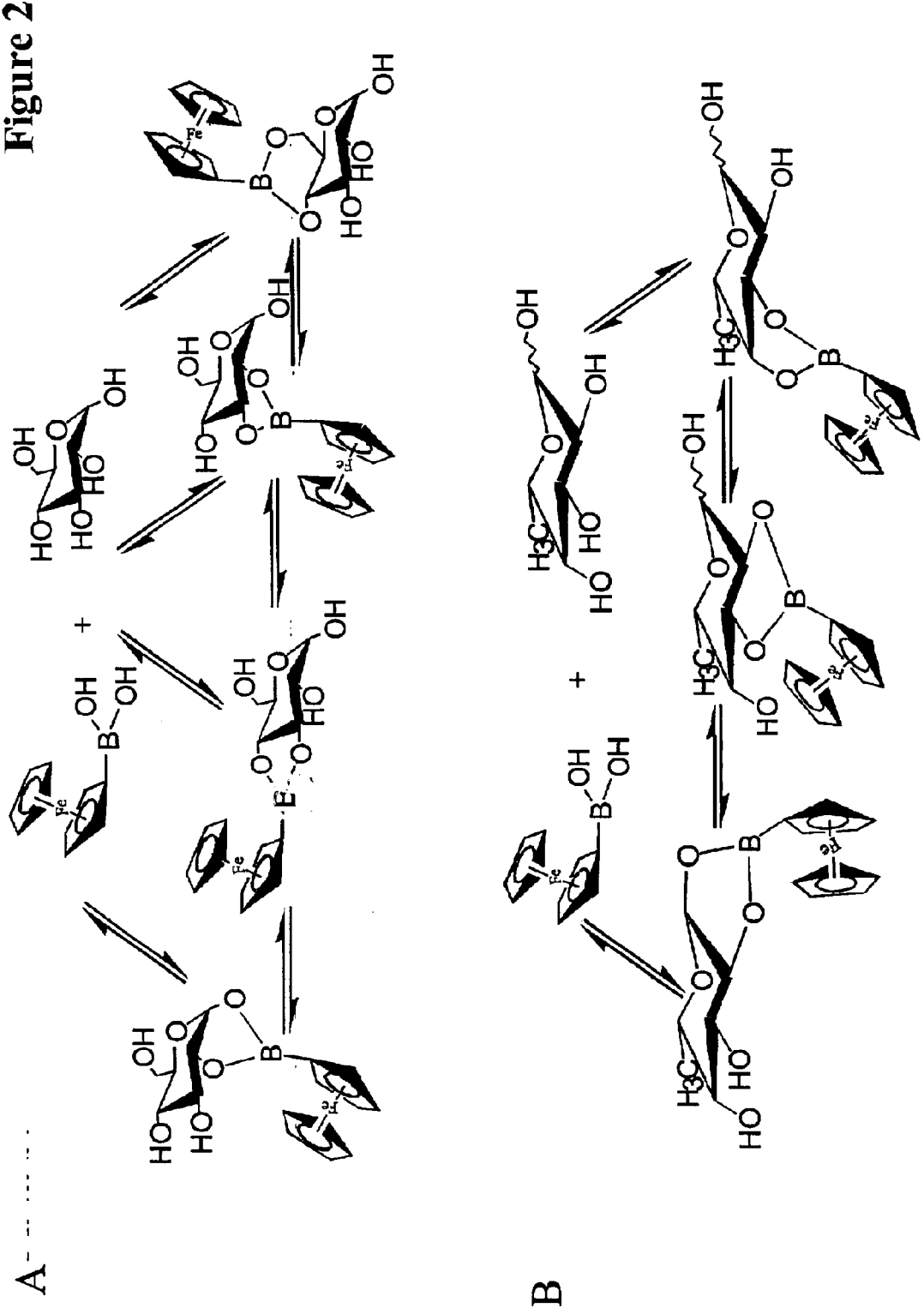
FIG. 2 is a schematic diagram showing the liquid phase equilibrium derived from the addition of excess FcBor with D-Glc and L-Fuc.
Figure 3:
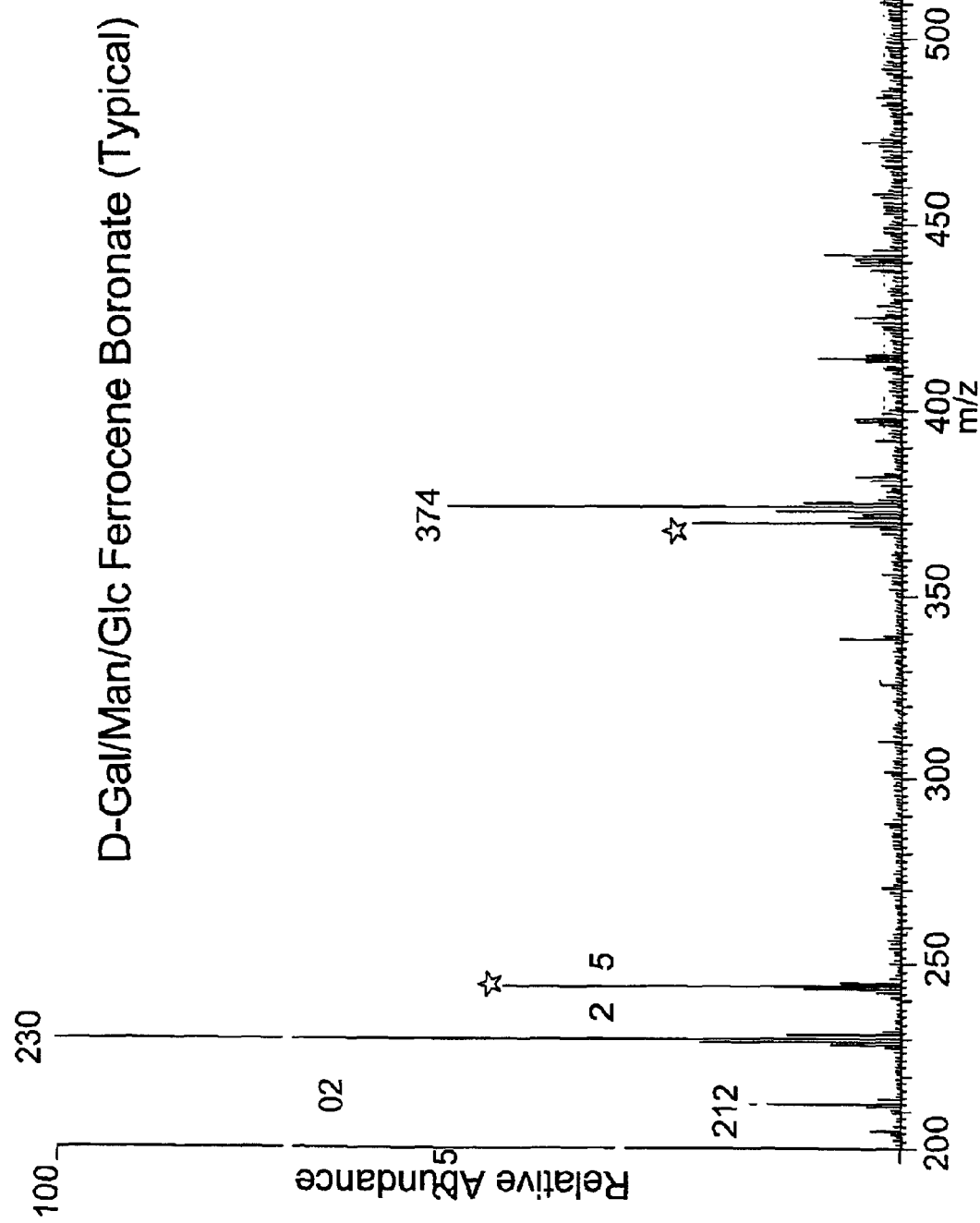
FIG. 3 is a schematic diagram showing an ion spectrum of D-Man which is a typical representation of the FcBor derivatized monosaccharides.

FIG. 1 shows the ECC modified electrospray v-device that is used to provide an efficient single electron oxidation of the ferrocene boronate carbohydrate esters. Derivatization take place at mM or lower concentration in non-aqueous solutions composed of MeCN with a small percentage of DCM added (ca 10%). The derivatization takes place in situ upon dilution from stock solutions. The derivatization process is able to proceed with any pair of suitable primary (1°-OH) or secondary hydroxyl groups (2°-OH), of a typical monosaccharide (FIG. 2). The c-$F_cBors$ are formed with either a five-member or six-member ring system. The 2°-OH viscinal diols displaying suitable paired equatorial/ equatorial (e/e) geometry make good candidates for this chemistry. However, it has been shown that the stereochemistry of the 1°-OH at C-6 and a suitable equatorial or axial 4-hydroxyl may also be derivatized forming a six member ring c-$F_cBor$ (FIG. 2.) The resultant typical molecular ion derived from D-Man after reaction with $F_cBor$ is shown in FIG. 3.

Figure 4:
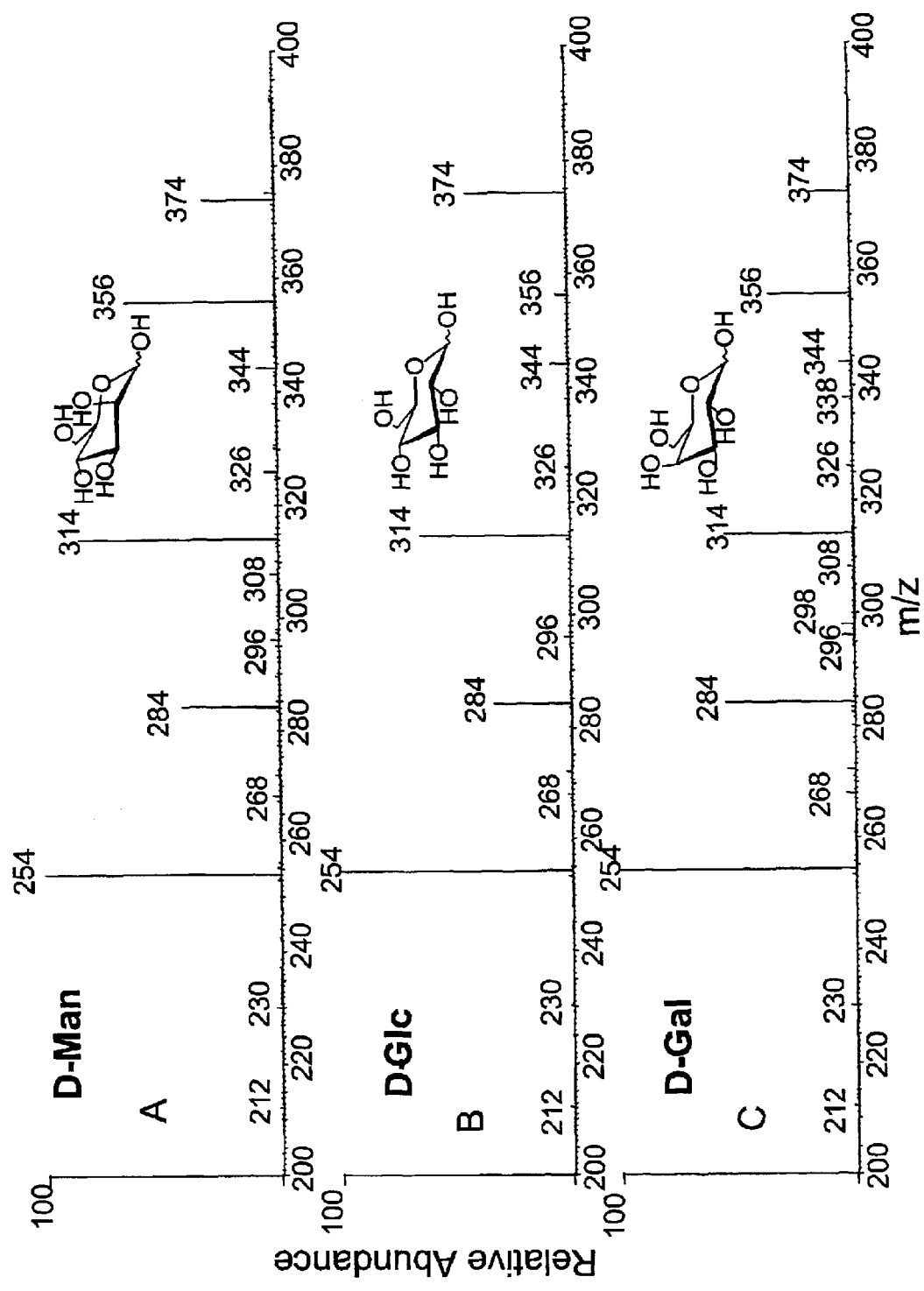
FIG. 4 is a schematic diagram showing the comparative $MS^2$ spectra for three biologically important epimers of D-Man; D-Glc and D-Gal.
Figure 5:
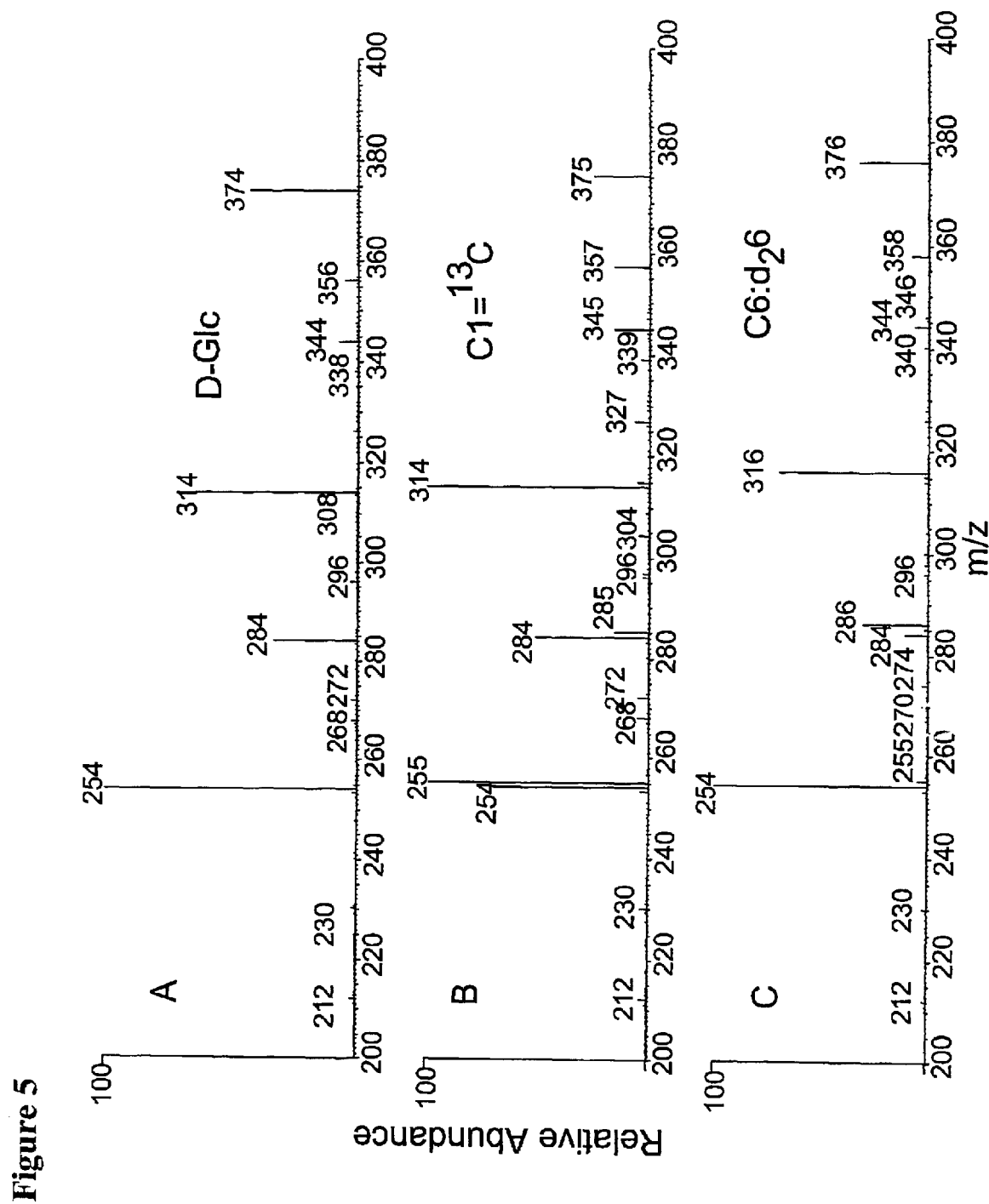
FIG. 5 is a schematic diagram showing the comparative $MS^2$ spectra for two isotopically enriched samples of D-Glc.
Figure 6:
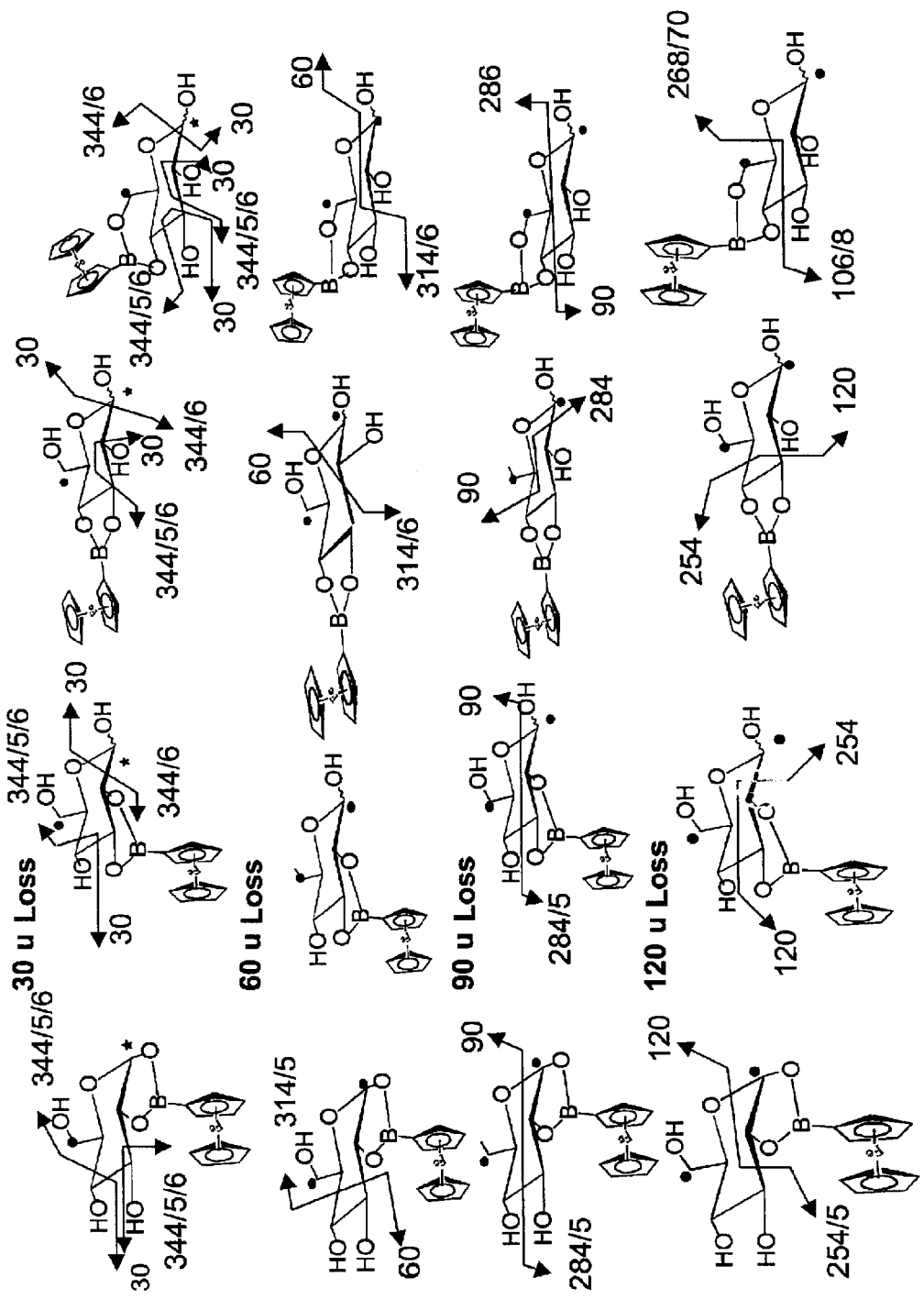
FIG. 6 is a schematic diagram showing four c-FcBor complexes possible from the derivatization of D-Glc using FcBor.
Figure 7:
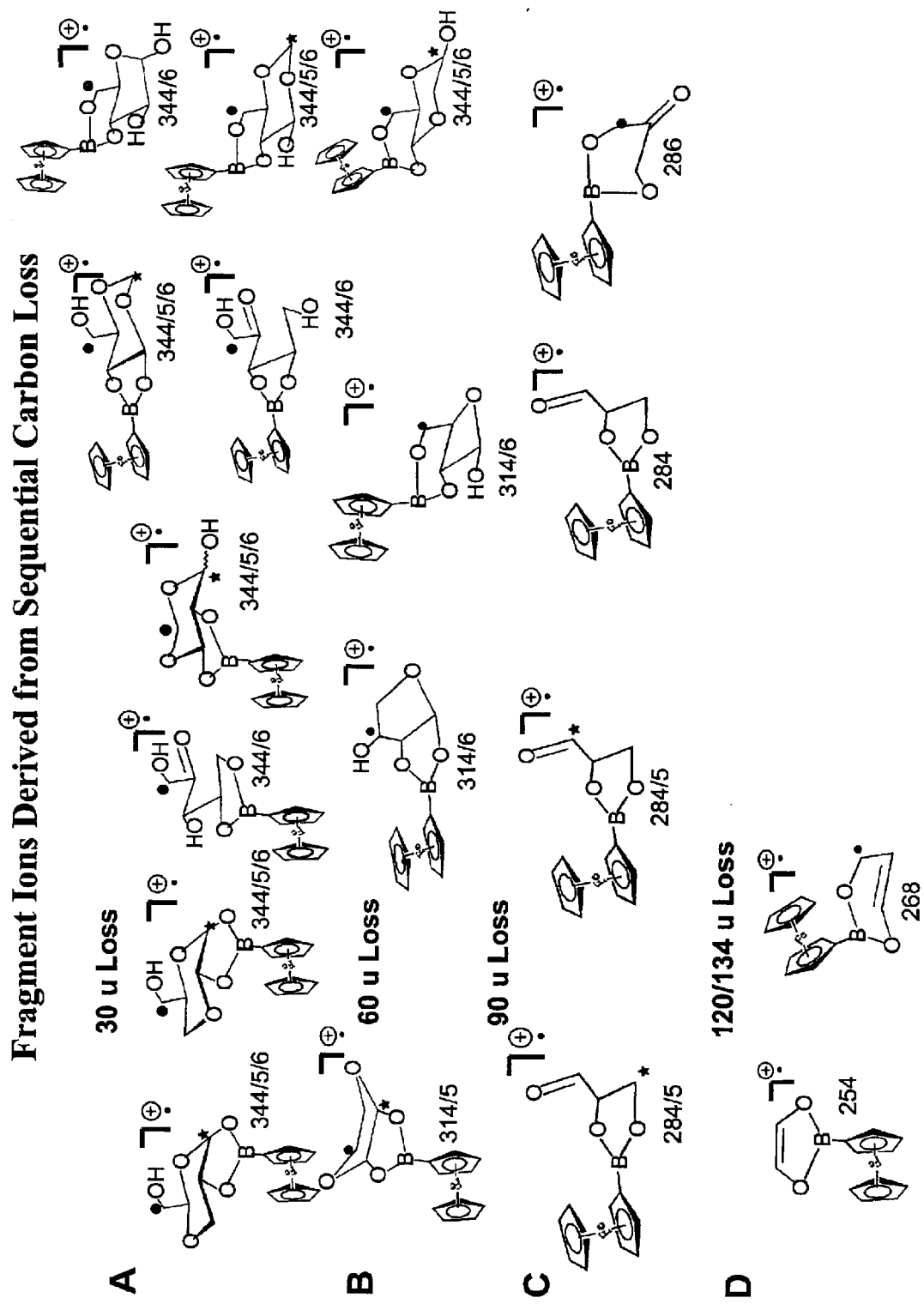
FIG. 7 is a schematic diagram showing the possible structures of ions generated by neutral losses of 30, 60, 90 and 120/134 mass units during cross ring fragmentation of c-FcBor complexes.
Figure 8:
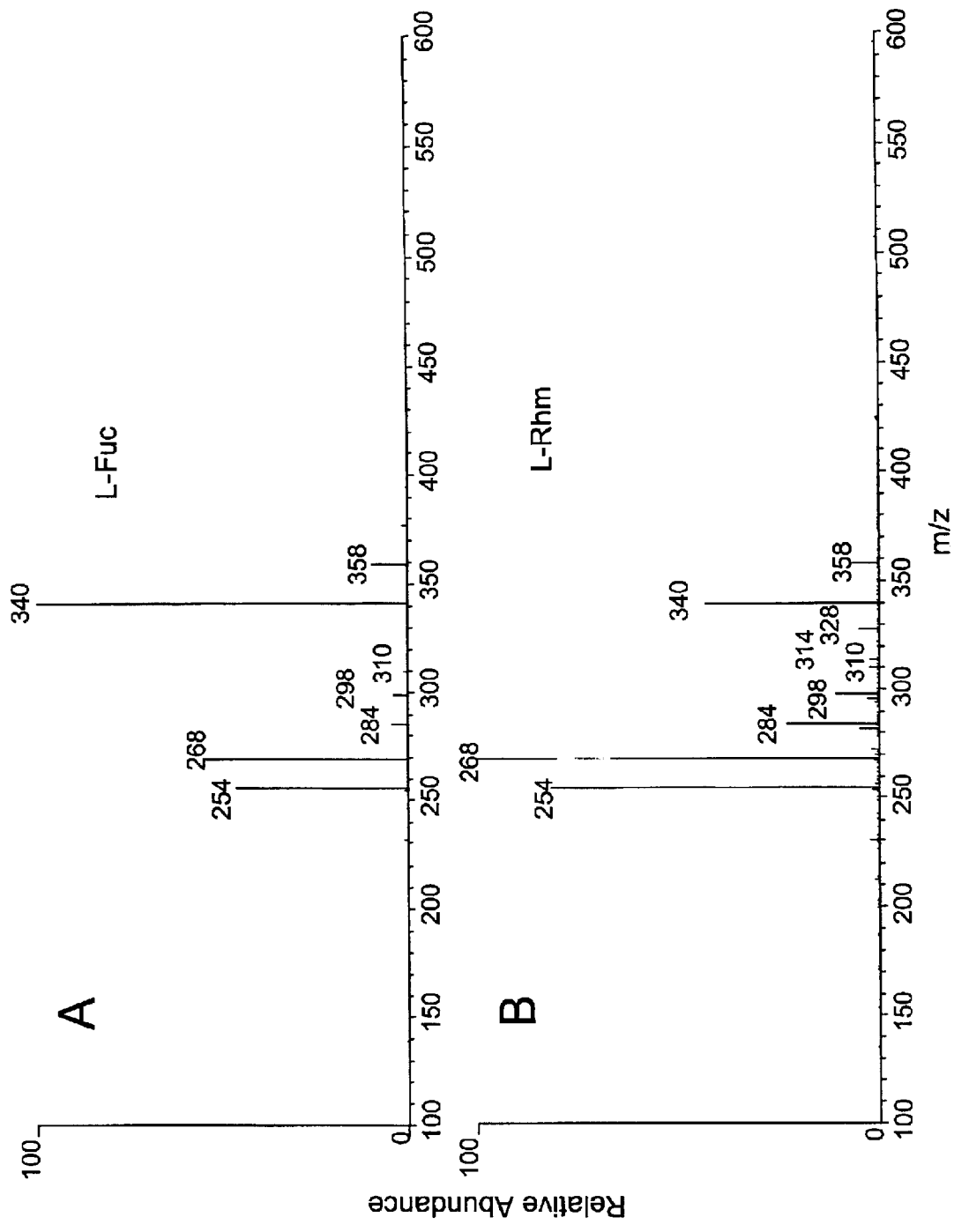
FIG. 8 is a schematic diagram showing the $MS^2$ spectra derived from the parent m/z 358 ion at 27% collision energy of L-Fuc and L-Rhm.
Figure 9:
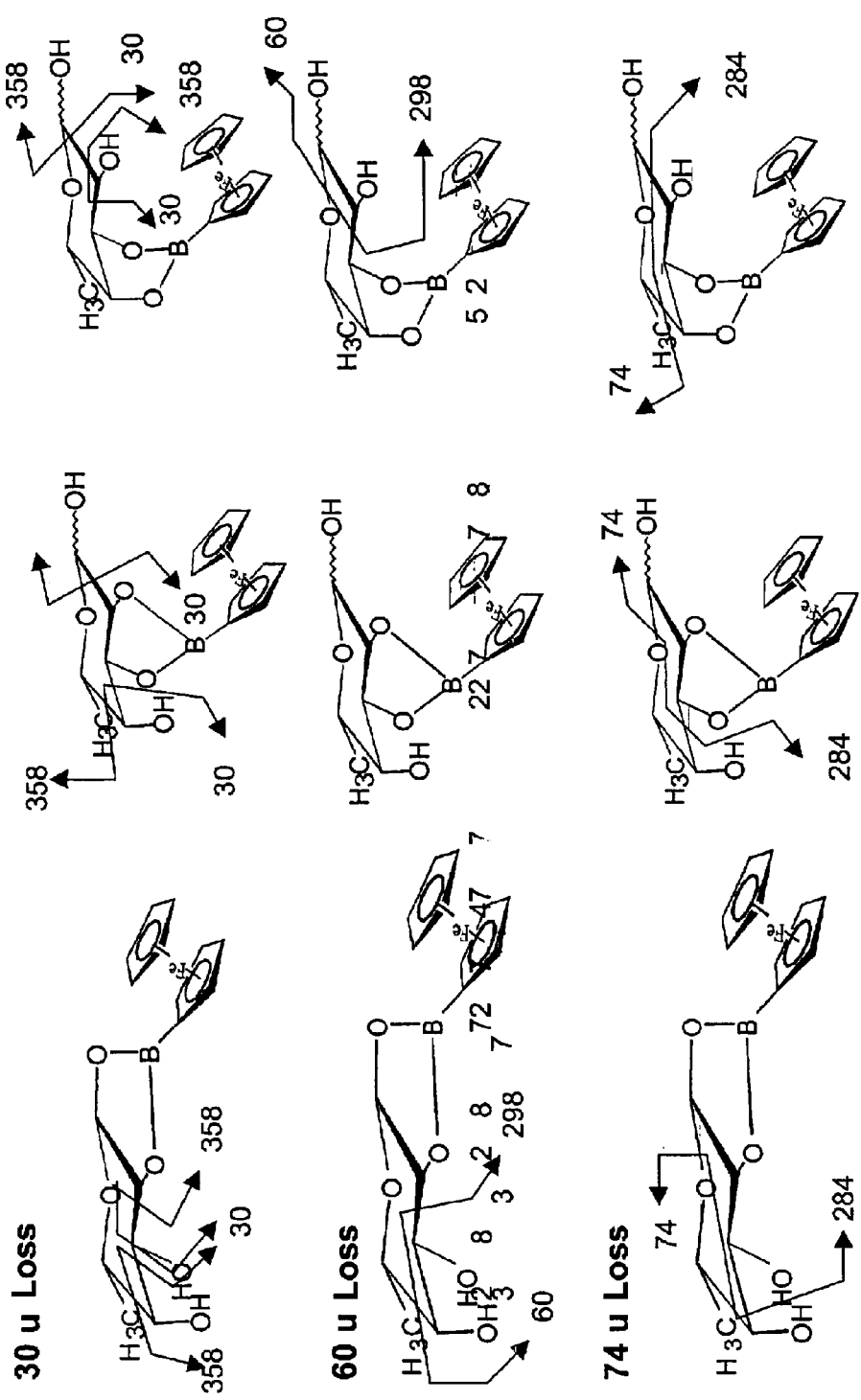
FIG. 9 is a schematic diagram showing the possible routes of fragmentation for L-Fuc.
Figure 10:
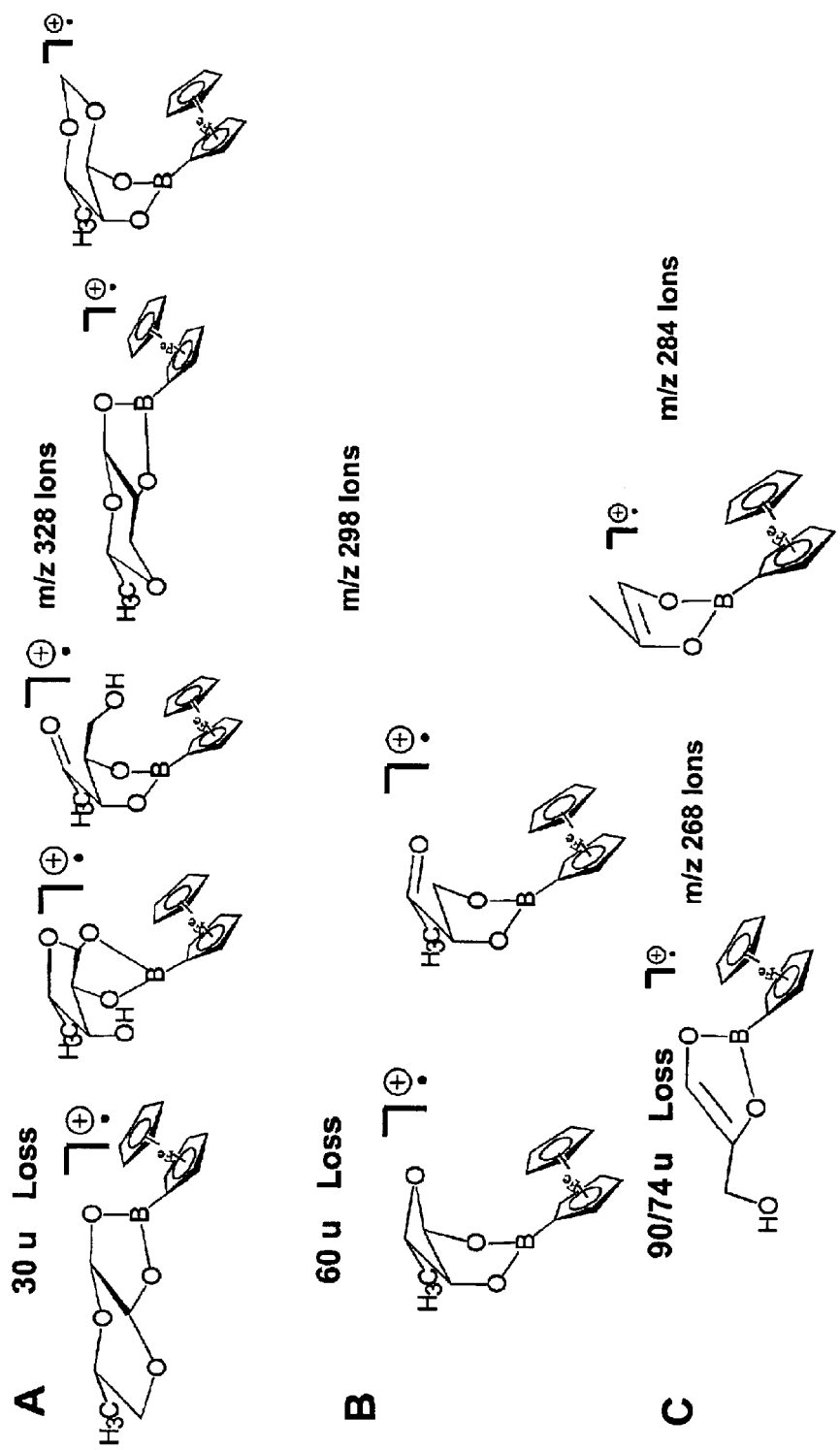
FIG. 10 is a schematic diagram showing the possible significant ions derived from the neutral loss of 30, 60, 90 or 74 u.

A comparison of the $MS^2$ spectra for the three biologically important epimers of D-Glc shows that each isomer produces a unique reproducible spectrum at the same relative collision energy of 27%. The comparative $MS^2$ data for D-Glc, D-Gal and D-Man appears in FIG. 4. The fragment ions produced are derived from a small group of possible precursor compounds in which multiple equilibria exist (FIG. 2). Collisionally induced dissociation (CID) in the ion-trap MS results in a series of fragment ions which represents the successive losses of formaldehyde (30 u) and water (18 u). A full compliment of cross pyranose ring fragments exists wherever the position of the cyclic ester will allow. The diagnostic ions for the c-$Fe_cBors$ are m/z 254 and m/z 268 (FIG. 5). These species are thought to result from the two residual carbon atoms after all four others have been lost as neutral fragments. The use of isotopically labeled D-Glc has allowed some insights into the possible nature of the precursor compounds and some of the probable fragmentation pathways. The comparative data from double deuterium labeling at the C-6 methylene and $^{13}C$ labeling at C-1 are shown in FIG. 5. The proposed fragmentation scheme and the resultant significant ions for D-Glc are shown in FIGS. 6 & 7. As fragmentation of the pyranose ring is dictated by the relative degree of derivatization of successive diol pairs, all possible cross ring fragments are represented. The ratios of the important ions resulting from successive 30 mass unit losses (m/z 344, 314, 284) to the residual m/z 254 differentiate between the isobaric structurally related epimers of glucose. The ratio of these significant carbon losses compared to the defining m/z 254 ion provides a recognition tool for each monosaccharide. Visual examination of the spectra show that the ease of initial water loss (resulting in m/z 356) is noticeably different between the three Glc epimers. Most abundant m/z 356 ion is obtained from the product ions of the D-Man epimer and least from D-Glc (with no axial hydroxyl groups). The ability to lose both water and the first carbon atom, (as HCHO) producing m/z 356 and m/z 344 appears to be affected by the relative stereochemistry of the 2° OH groups. Since the propensity to form a cyclic ester varies between the different epimers, the populations of derivatives differ, and consequently the patterns of fragmentation observed differ. The two C-6 deoxymonosaccharides L-Fuc and L-Rhm produce easily differentiable $MS^2$ spectra as seen in FIG. 8. The selected molecular ion (m/z 358) produces the usual and abundant m/z 254 diagnostic ion after available carbons have been stripped (as HCHO) from the 6-deoxypyranose ring. The C-6 carbon is lost during cross pyranose ring fragmentation as a neutral fragment (74 u) giving anion of m/z 284. FIGS. 9 and 10 show the possible cross ring fragmentation routes and the resultant ions generated. Sequential loss of water also produces a recognizable sequence of ions similar to the D-Glc epimers. Interestingly, only L-Rhm shows a loss of one carbon atom, (−30μ as HCHO), by producing m/z 328. L-Fuc prefers to lose a two-carbon fragment to if produce m/z 298. In this way, L-Fuc may be easily distinguished from L-Rhm. Substitution at various positions on the pyranose ring in either the D-series hexoses or the L-series will dictate the fragmentation patterns seen with disaccharides and higher oligosaccharides.

Figure 11:
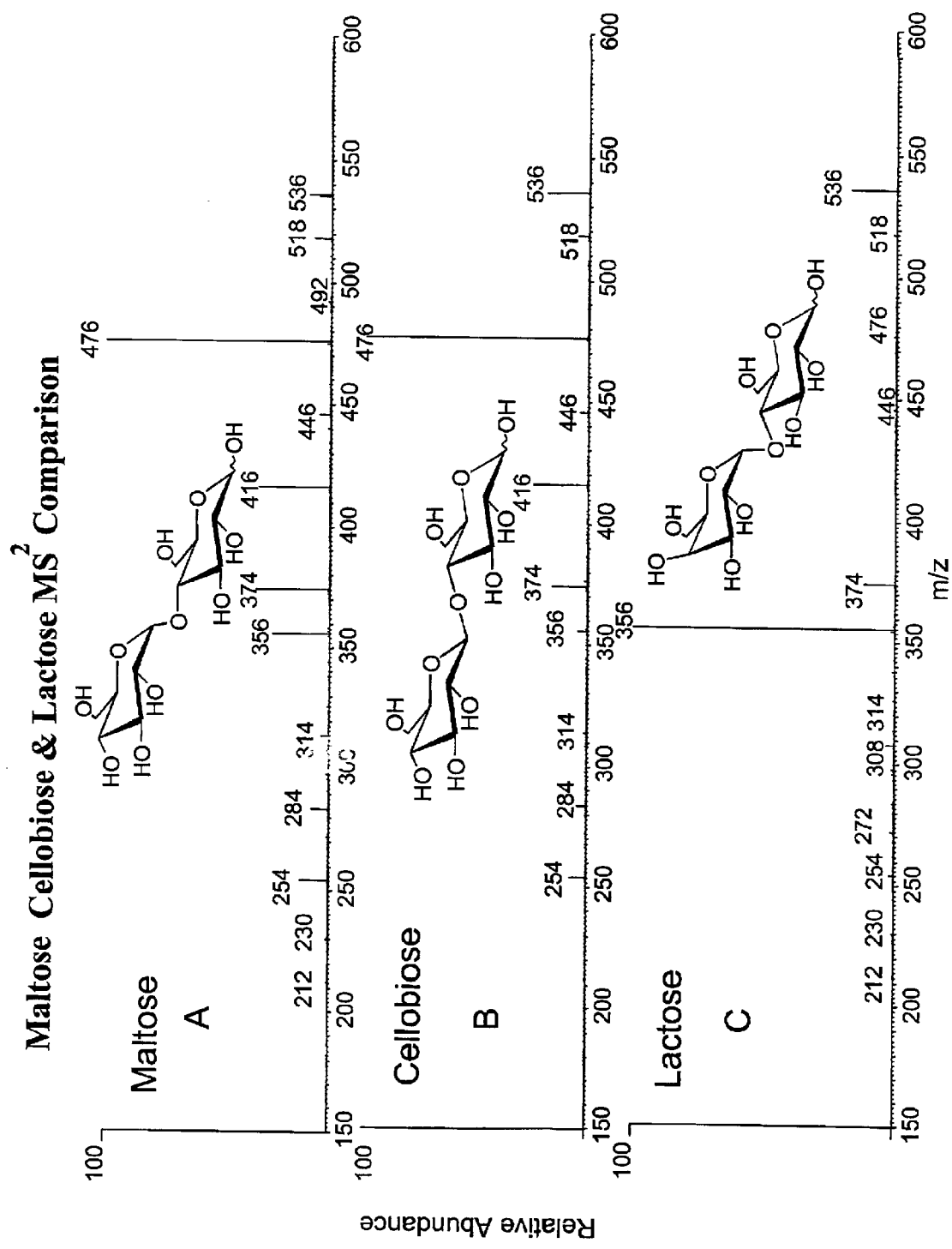
FIG. 11 is a schematic diagram showing the comparative $MS^2$ spectra of maltose, cellobiose, and lactose.

A comparison was made between three typical disaccharides (A) maltose {b-D-Glc-(1–4)-D-Glc}, (B) cellobiose {a-D-Glc-(1–4)D-Glc} and (C) lactose {b-D-Gal-(1–4)-D-Glc}. The first two disaccharides were chosen because they differ only in their anomericity. The stereochemistry around the non-reducing terminal of each Glc is b for cellobiose and a for maltose. As seen in FIG. 11, the $MS^2$ spectra for A and B are almost identical except for the relative abundance of the ions which directly result from the relative stereochemistry of either anomer. The m/z 374 represents the loss of one D-Glc hexose and the subsequent loss of 18 u to produce m/z 356. The stereochemistry at this point controls the ability to eliminate water providing the observable difference in relative abundance of these two ions. A comparison of maltose and lactose shows differences that are less subtle. Unlike maltose, the fragmentation of lactose is completely dominated by the bisection of the molecule and its subsequent loss of water leaving m/z 356 as the 100% ion. The predisposition toward this ion may be attributed to the cross ring assistance of the axial C-4 substituent of D-Gal, in lactose.

EXAMPLE 2

Figure 12:
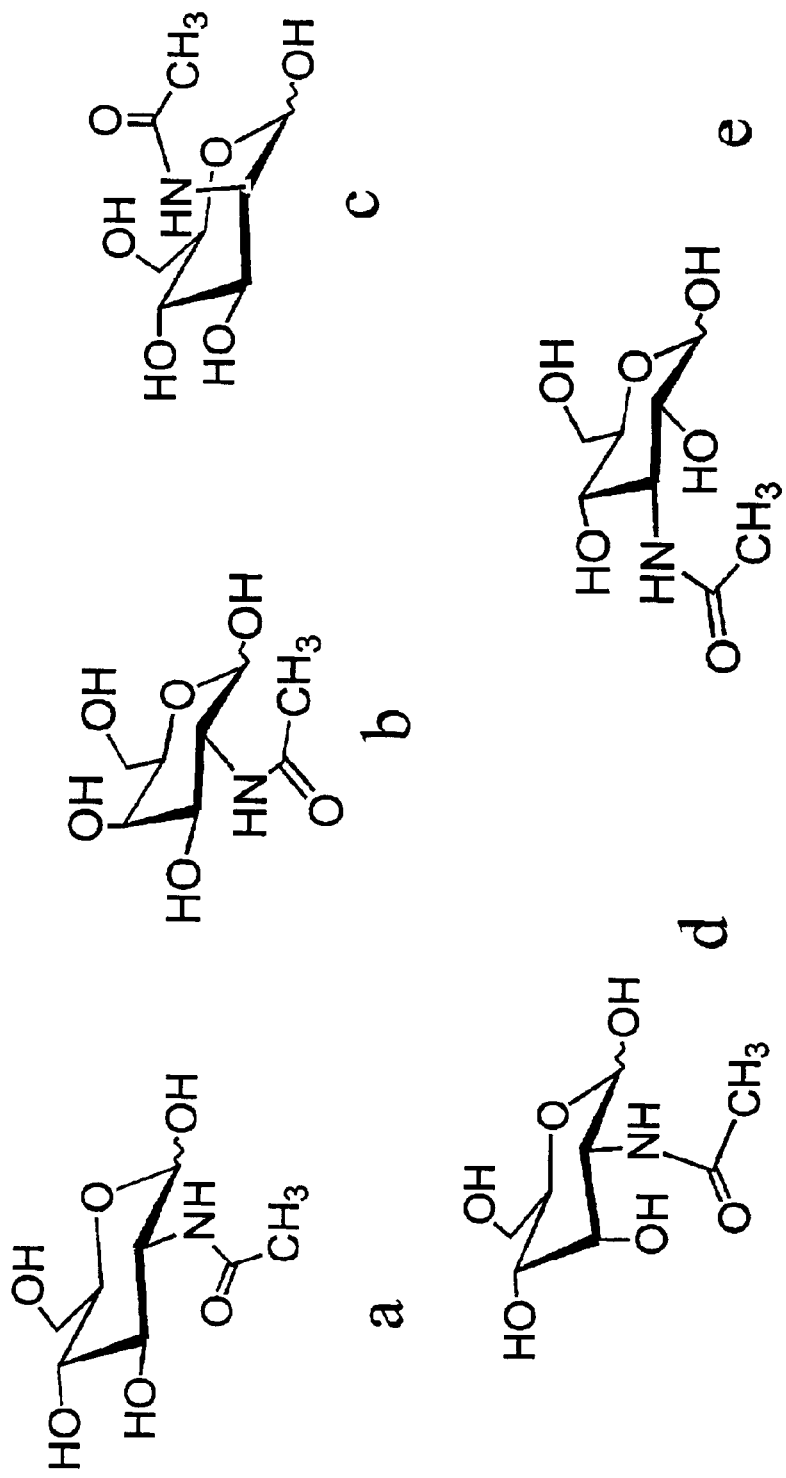
FIG. 12 shows the chemical structures of the hexosamine sugars examined: a) N-acetyl-D-glucosamine, b) N-acetyl-D-galactosamine, c) N-acetyl-D-manosamine, d) N-acetyl-D-allosamine, e) 3-acetamido-3-deoxy-D-glucose.
Figure 13:
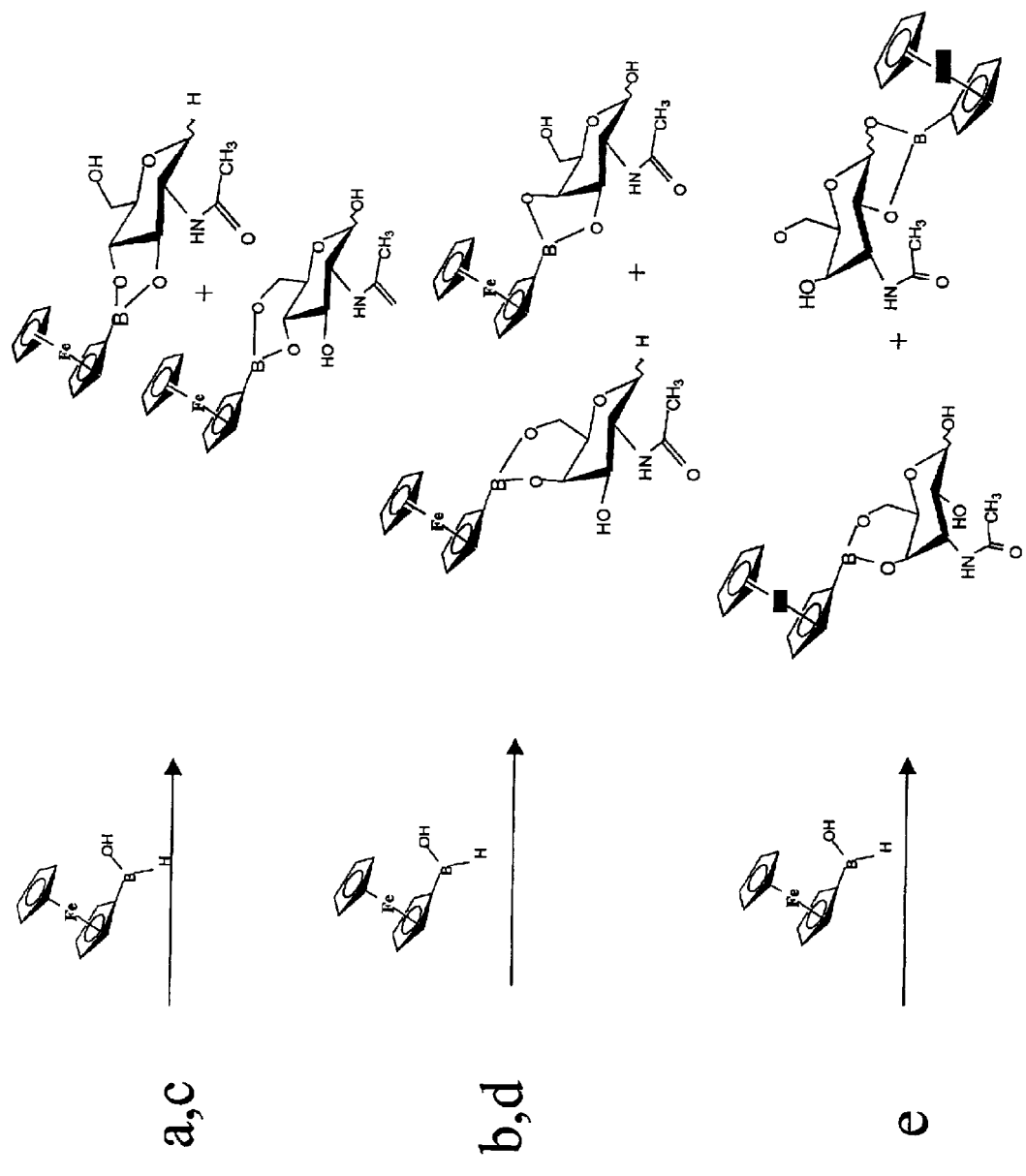
FIG. 13 shows that suitably positioned hydroxyl groups are derivatized with ferrocene boronate to produce five or six member cyclic ferrocenyl boronate esters. Hexosamines a and c have two suitable pairs, equatorial C3 & 4 and the C4 & 6 hydroxyls. Analytes b and d provide C4 & 6 and also the equatorial and axial hydroxyls at C3 and C4 respectively. Analyte e also provides the C4 & C6 hydroxyl, but C3 is blocked by the acetamido group, allowing derivatization of the equatorial hydroxyls of C1 & C2.
Figure 14:
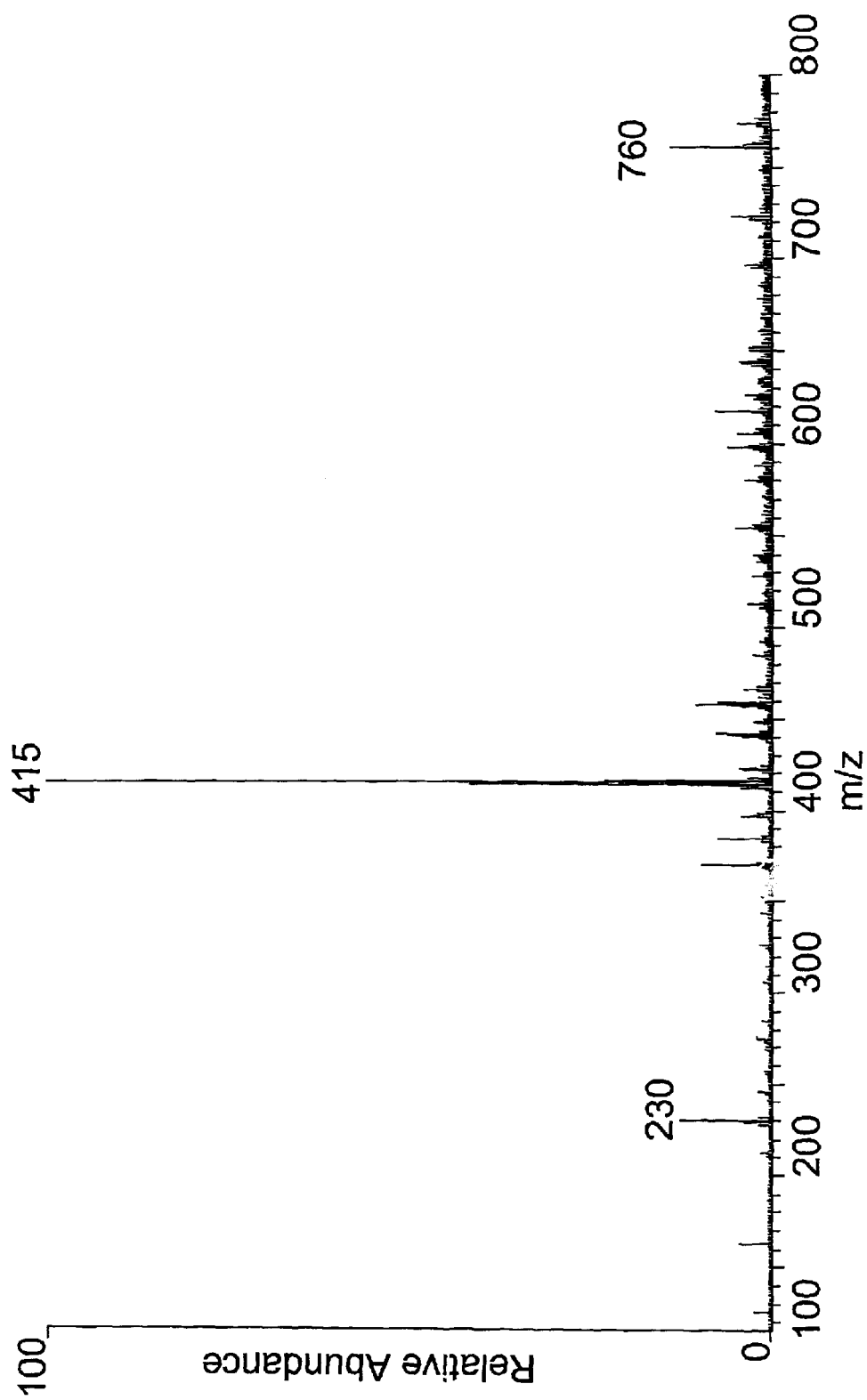
FIG. 14 is a full scan mass spectrum of a typical hexosamine derivatized using ferrocene boronate and electrosprayed using a continuous current flow cell. Molecular ions are generated from the derivatization process appear at m/z 415.2. The free derivatizing agent is also observed at m/z 230.2. The identity of the ion observed at m/z 760.9, with approximately 20% relative abundance, has not been established.

FIG. 12 shows the structures of N-acetyl amino sugars examined by ferrocenyl boronation and tandem ES-MS. Depending on the spatial availability of accessible hydroxyl groups presented by a given pyranose hexosamine, two possible isomeric c-$F_cBor$ esters can be formed (FIG. 13). Both five and six member ring c-$F_cBor$ esters are assumed to exist. The full-scan mass spectrum of a typical hexosamine produces a molecular ion centered at m/z 415 as shown in FIG. 14. The ion-cluster displays contributions derived from both boron and iron in terms of their isotopic distributions.

Using tandem MS for selective fragmentation of the m/z 415 molecular ion for hexosamines, $MS^2$ spectra are produced which are notably different from one another. All five hexosamine spectra share fragment-ions in common (as shown in FIGS. 15a–e). However, the ion m/z 296 is almost non-existent in GalNAc and 3-acetamido-3-deoxy-D-glucose (3GlcNAc), while it exhibits up to 20% relative abundance in the other sugars. The ion m/z 361 is also almost non-existent in GalNAc and 3GlcNAc but is present at up to 20% relative abundance in the other sugars. These grossly differing features, and the other major differences observed in relative ion abundance, make GalNAc and 3GlcNAc the most easily distinguished hexosamines.

Figure 15A:
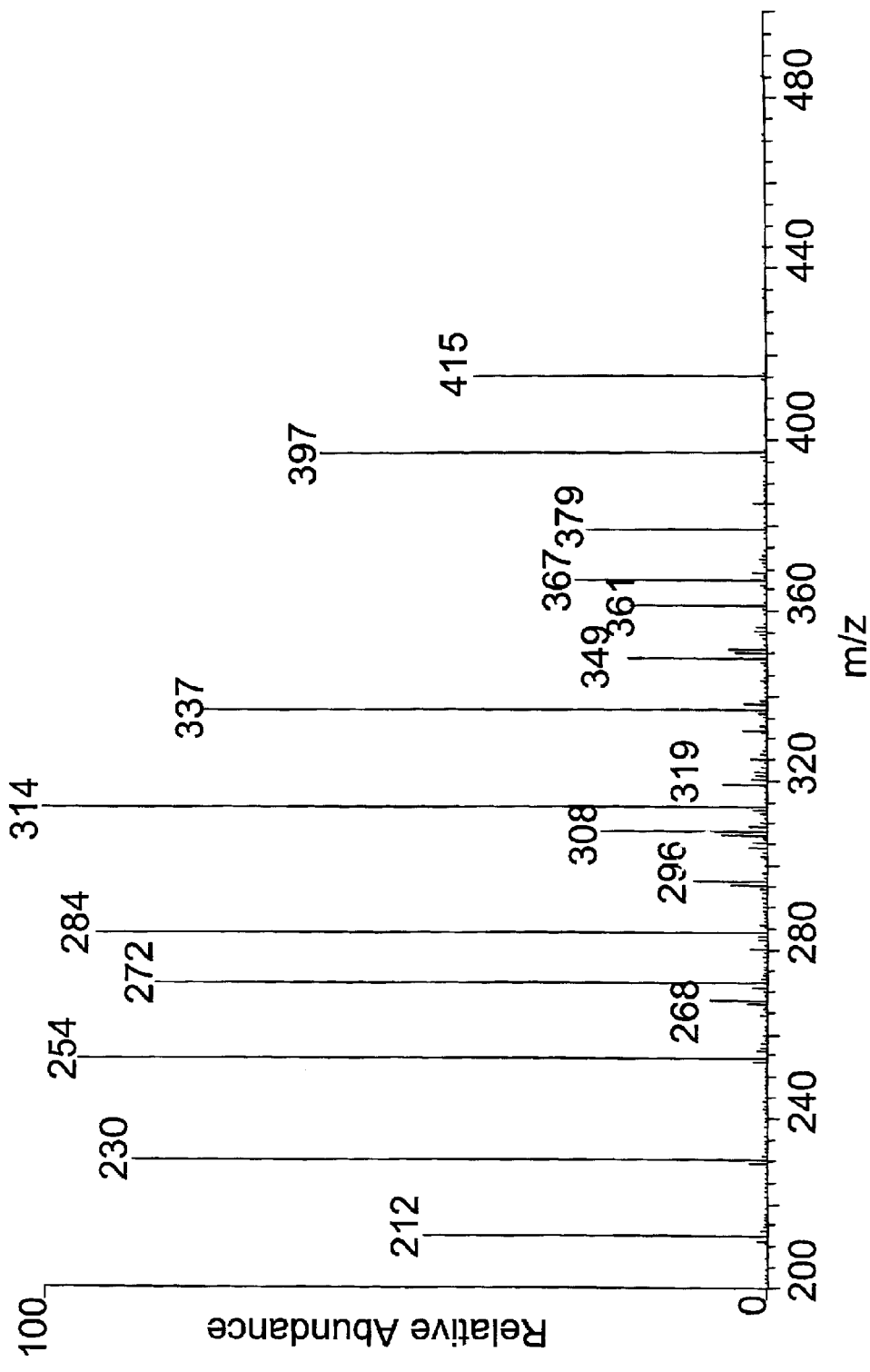
FIG. 15 shows that selected fragmentation of the m/z 415 ion of the studied N-acetyl hexosamines produces clearly defined fragmentation patterns. A) GlcNAc, B) GalNAc, C) ManNAc, D) AllNAc, E) 3-D-GlcNAc, F) $^{13}C$ labeled C1 of 3-D-GlcNAc.
Figure 15B:
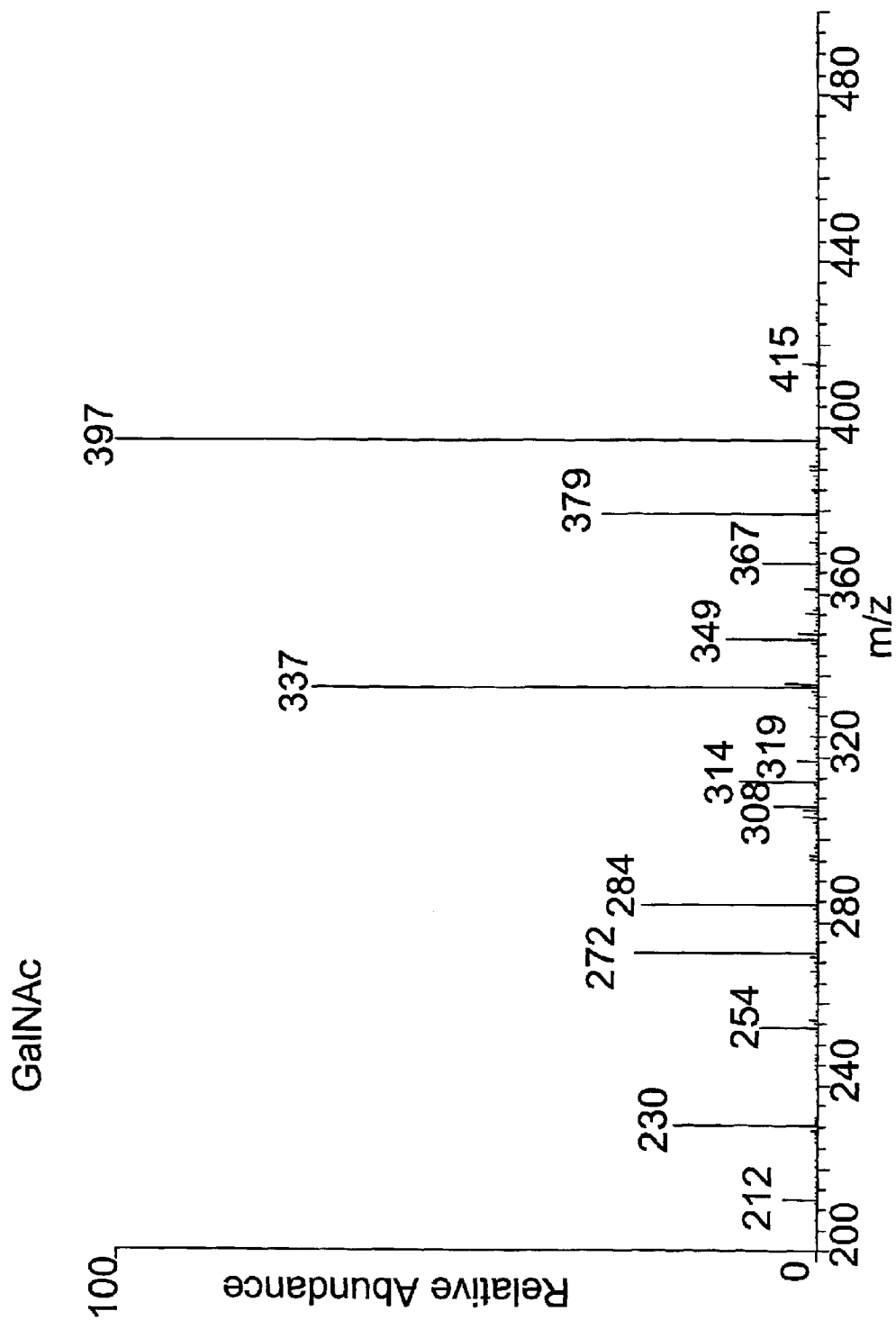
Figure 15C:
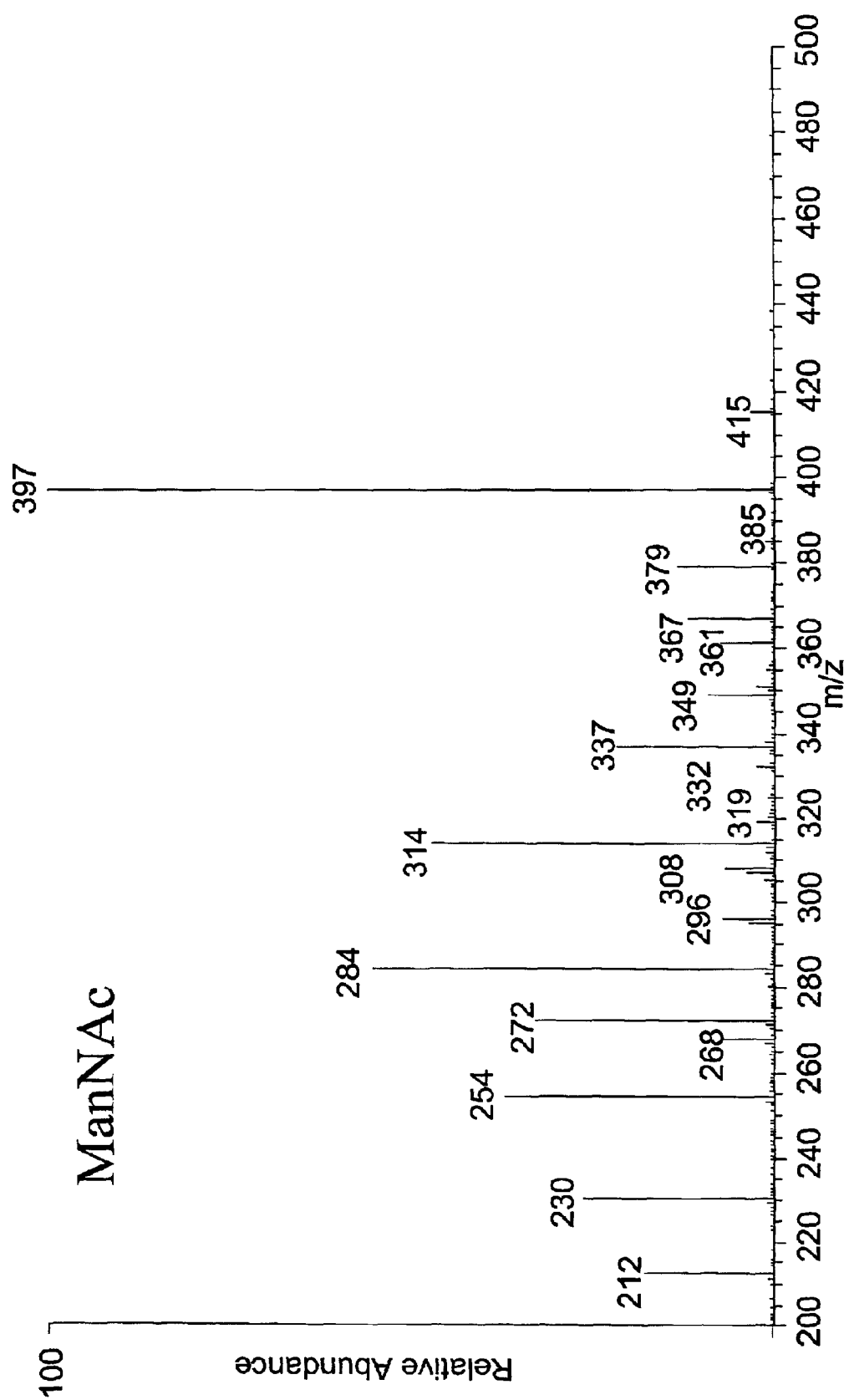
Figure 15D:
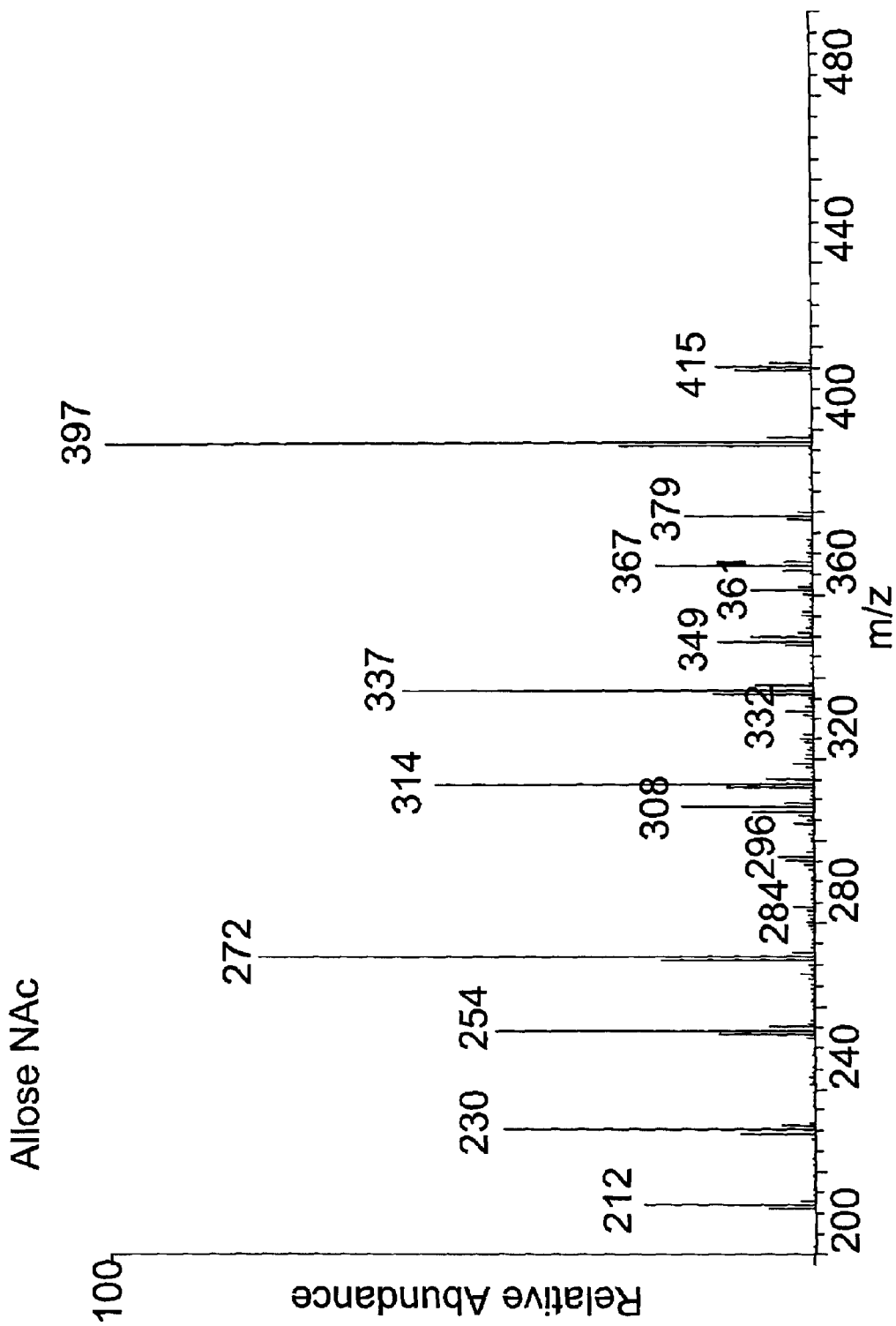
Figure 15E:
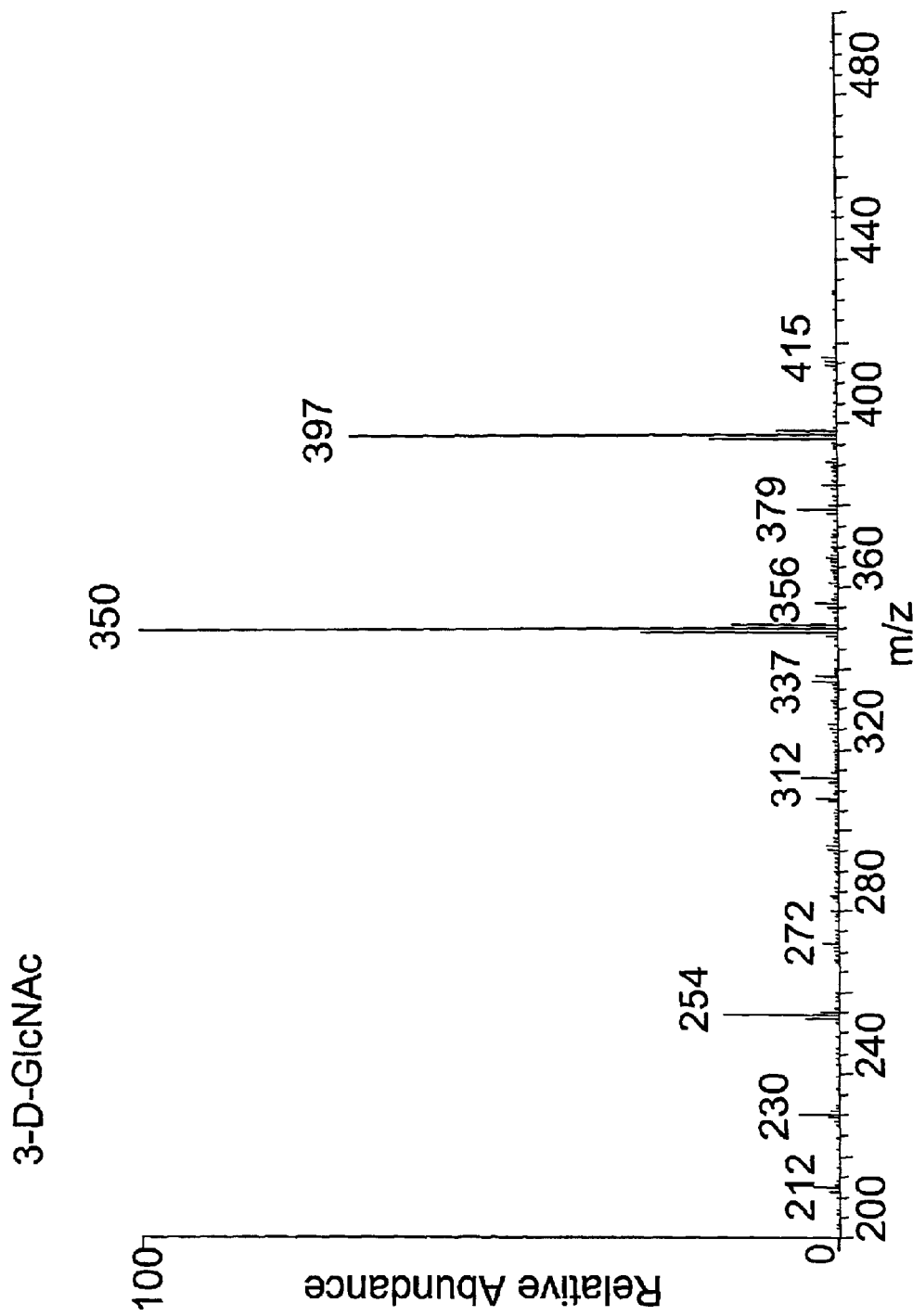
Figure 16:
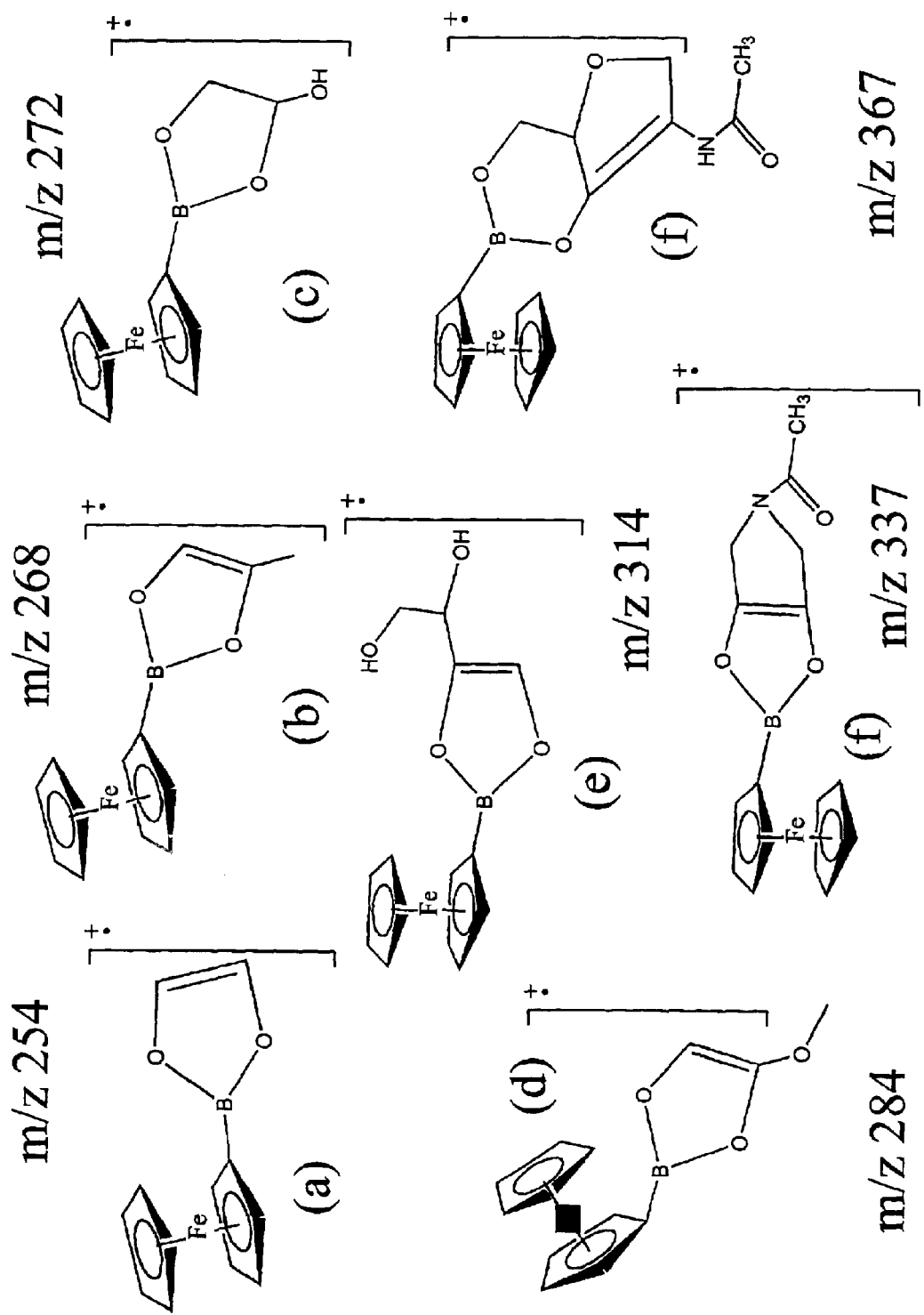
FIG. 16 shows that the selected fragments represent some of the possibilities for cross ring fragmentation of the N-acetyl hexosamines. The particular stereochemical orientation of the hydroxyl groups on each compound determines the relative abundance observed for each fragment ion derived from the selected molecular ion. It is expected that internal rearrangements of the original fragment will take place to provide delocalized species involving the cyclic boronate and the ferrocene ring systems as low energy systems.

The ions m/z 230 and 212 are normally present and are derived from the loss of ferrocenyl boronate from the sugar with concomitant water loss. The reporter-ion m/z 254/268 indicates that a five and or six member c-$F_c$Bor was present as shown in FIG. 16 (fragments a, b) proposed fragment ion structure. The ion m/z 254 appears to be very stable (presumably by electronic delocalization through the boron atom). The associated ions at m/z 272, 284, 314, 337 and 367 can all be rationalized as being formed from a cross pyranose ring fragmentation and subsequent rearrangement (FIGS. 16c, d, e, f, g). It is believed that the original stereochemistry of the pyranose ring has an effect on which subsequent rearrangements take place, and the various rearrangement pathways involved, dictate the relative abundance of these resultant ions. The spectra (FIGS. 15a–e) of all the hexosamines are based on early loss of water followed by sequential loss of ring carbons as formaldehyde (30 u.) The loss of a cyclopentadienyl ring, (66 u) with the production of ions centered at m/z 349/350 is present in all of the MS2 spectra, but most prominent in 3GlcNAc (FIG. 5e) where it dominates. Significant fragment ions m/z 272/284 are proposed as being generated by the ring boronic ester retaining a hydroxyl group while losing the entire remainder of the non-boronic ester structure.

A one mass unit shift from m/z 367 to an exclusive 368 (no m/z 367) is observed in the $^{13}$C (C1) isotopically labeled GlcNAc sample, FIG. 15f. Further comparisons of labeled to unlabeled spectra, show a one mass unit shift from m/z 337 to 338 in the labeled GlcNAc with approximately 8% retention of m/z 337. Ion's m/z 397 and 380 are also seen to retain the $^{13}$C label during the sequential loss of two water molecules. A minor ion, m/z 385/386 also appears to retain the label and indicates a 1C loss as HCHO from elsewhere in the GlcNAc molecule. The population distribution of pairs of cyclic boronate esters derived during esterification of a–d (FIG. 12) reveals stereochemical details of each hexosamine during tandem MS as a function of various key ion abundances. Under identical conditions, each hexosamine produces a characteristic set of ion intensities.

In compound e (FIG. 12), which represents the non-natural analog of the biologically significant epimers of GlcNAc due to substitution of the acetamido group at the three-position instead of the two-position, a completely different $MS^2$ spectrum arises. This spectrum is dominated by the simple loss of water and of a cyclopentadienyl ring (FIG. 15e). Many of the ions observed in the spectra of compounds a–d appear individually with only modest relative abundance but contribute significantly to the defining fragmentation pattern when taken as a whole.

EXAMPLE 3

Figure 17:
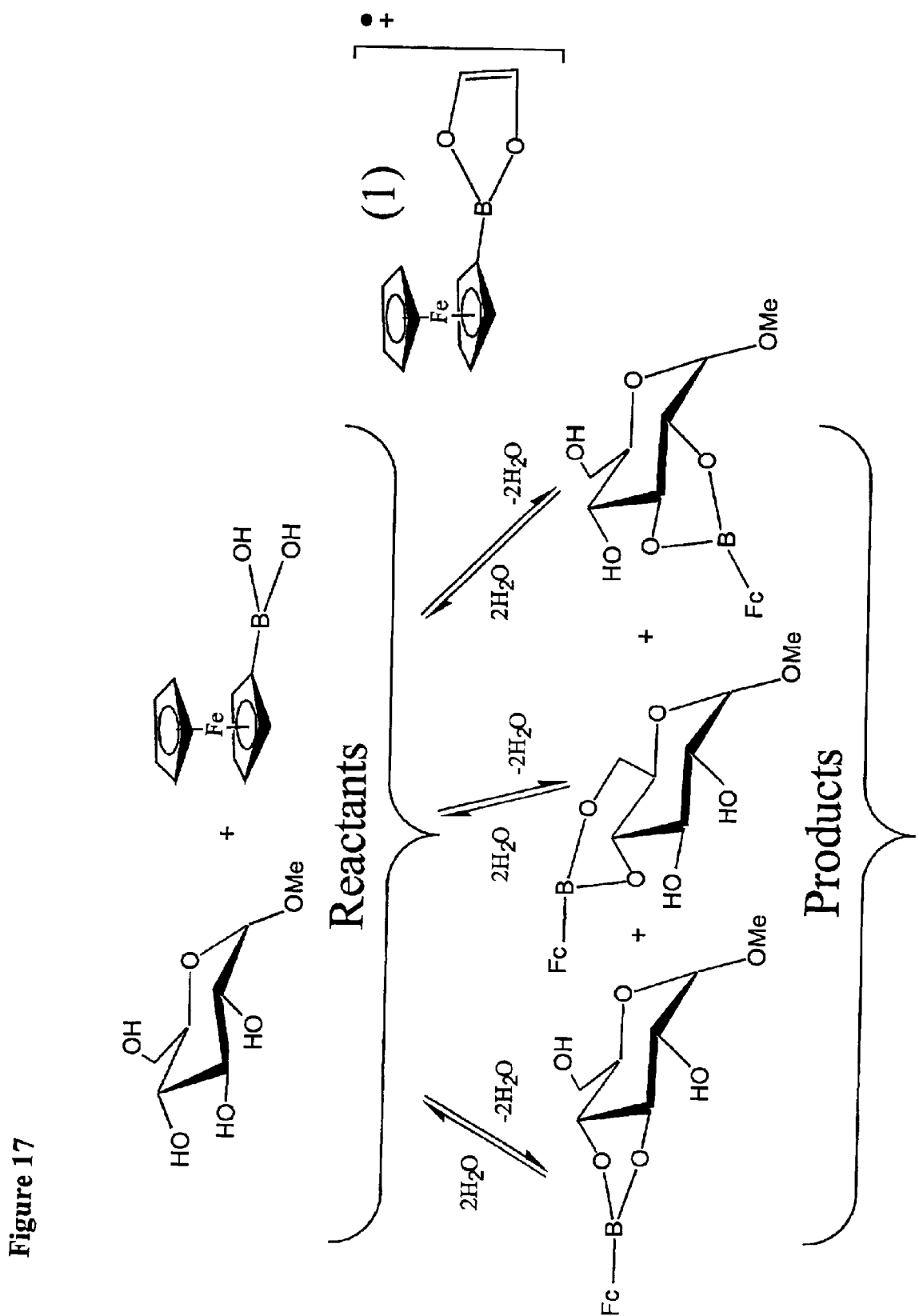
FIG. 17 is a schematic diagram showing a mechanism for generation of a population of was isobaric ferrocenyl boronate esters from alpha-o-methyl D-glucose.

Derivatization of suitable viscinal 1,2 or 1,3 diols proceeds as a reversible reaction at room temperature. The reaction scheme generates a reproducible distribution of isobaric analytes. It is believed that the reaction is driven in the forward direction during ES-MS. Contact of the vapor-phase reaction mixture with the heated stainless steel capillary of the mass spectrometer promotes the removal of solvent. Included in this process is water generated during boronate ester formation. This process tends to encourage the forward reaction, favoring products. FIG. 17 shows a proposed mechanism for the generation of a population of isobaric ferrocenyl boronate esters from α-O-methyl D-glucose. The reaction scheme models the results of ferrocenyl boronation for three anomeric pairs of O-methyl D-glycoside epimers. The isobaric population of molecular ions, m/z 388, are selected for CID.

Figure 18:
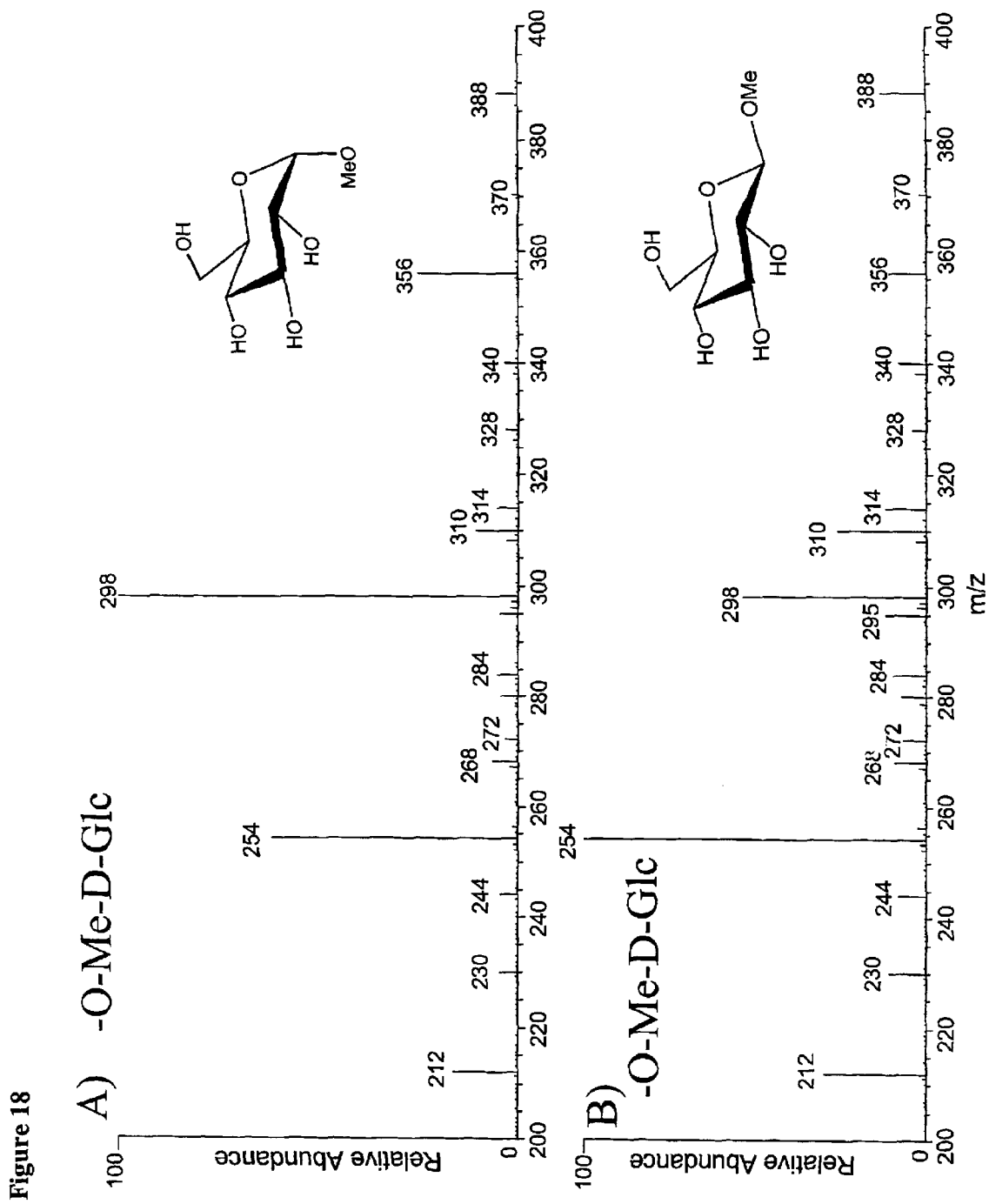
FIG. 18 is a schematic diagram showing α (A) and β (B) O-methyl glucosides derivatized as their ferrocenyl boronate esters. The $MS^2$ spectra represent the fragmentation of populations of all possible diastereomers formed during the reaction and electrosprayed under identical conditions. A distinct m/z fingerprint for each anomer is produced in terms of ion intensities.
Figure 19:
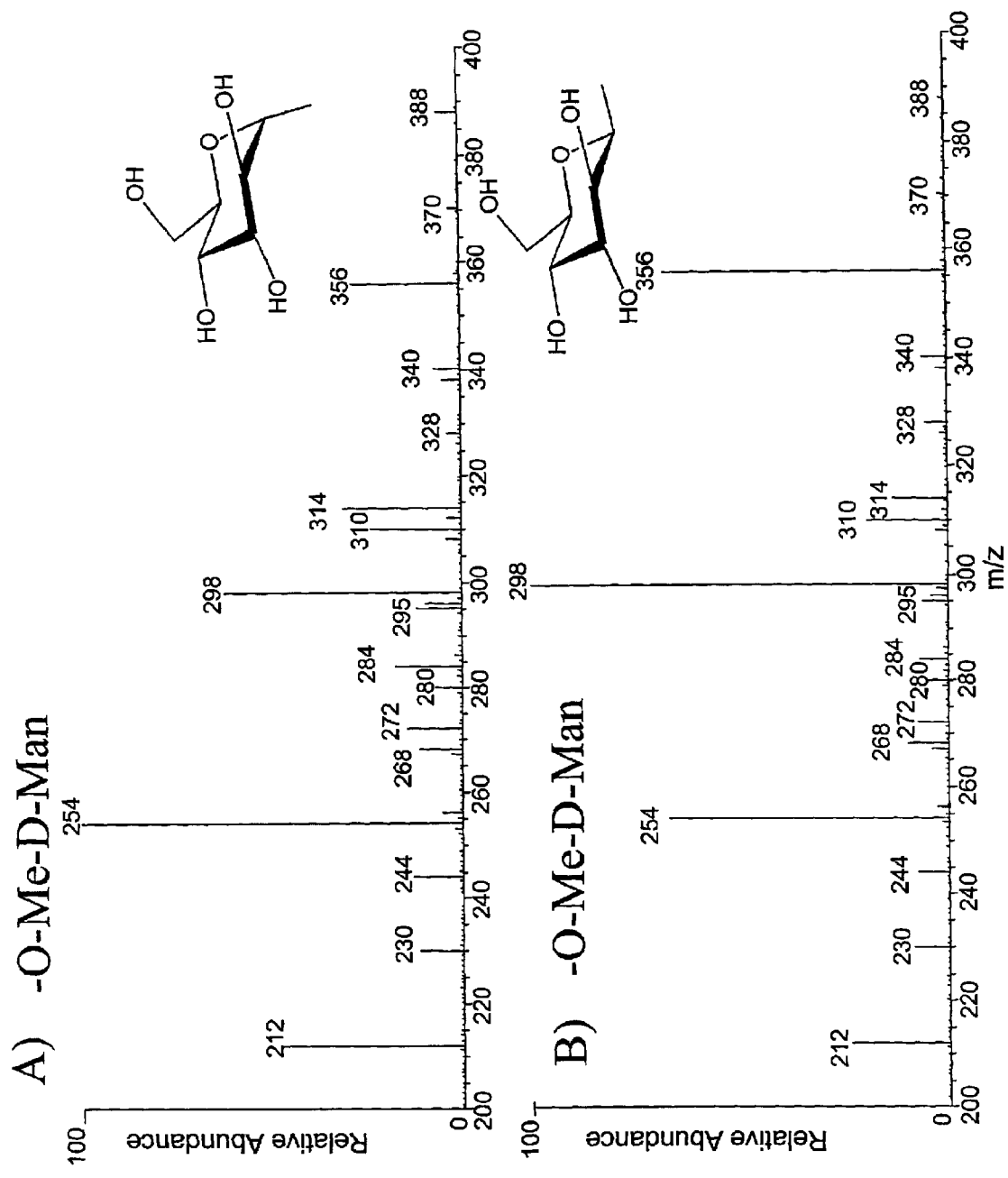
FIG. 19 is a schematic diagram showing α-O-methyl mannoside (A) and β-O-methyl mannoside (B).
Figure 20:
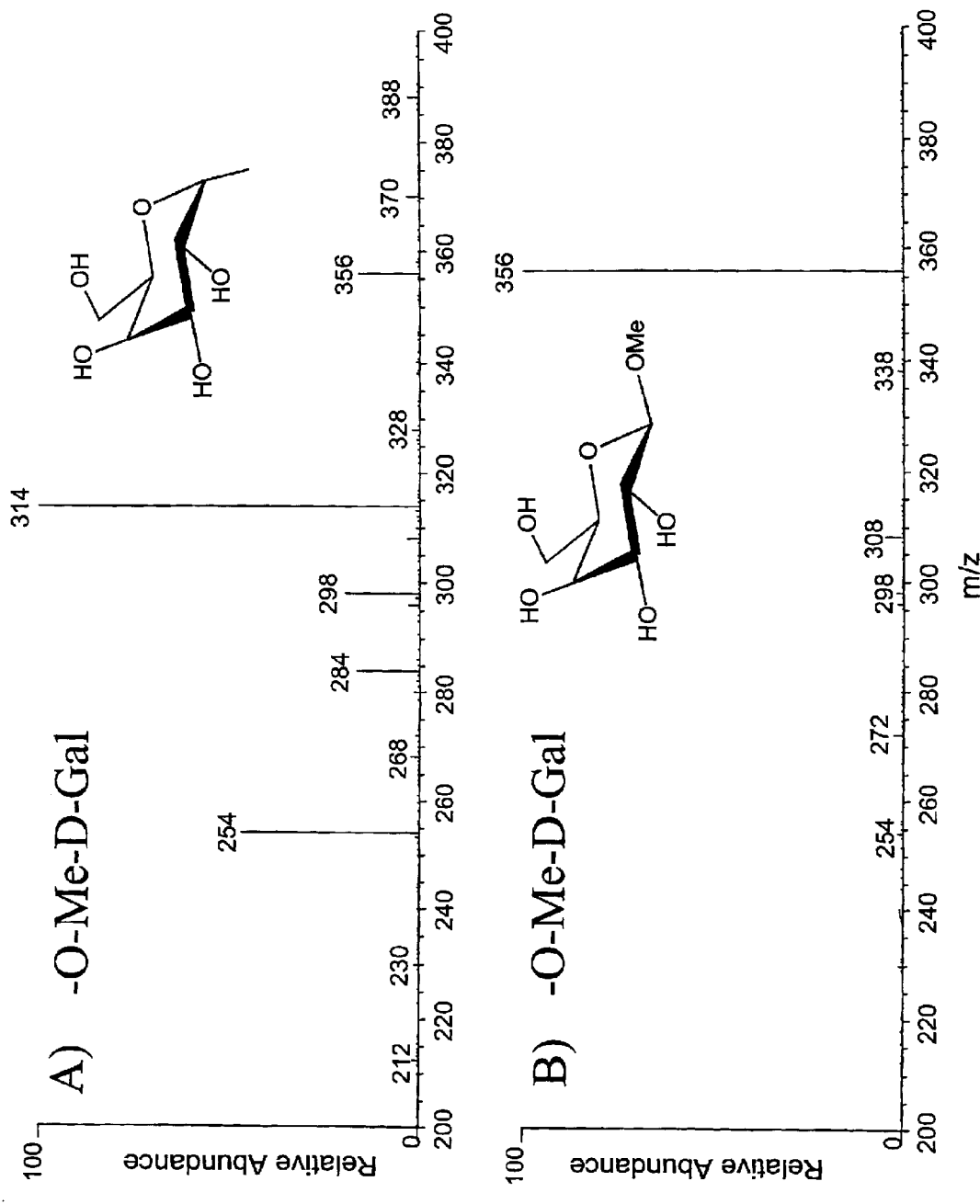
FIG. 20 is a schematic diagram showing β-O-methyl galactoside (A) and β-O-methyl galactoside (B).

The $MS^2$ spectra for each O-methyl glycoside were selected at m/z 388 as shown in FIG. 18. Acquisition was made at approximately the same concentration, 150 μM, and at the same collisional energy (25%). The m/z 254 ion is present in every spectrum and diagnostic for the presence of a viscinal diol. The ion is represented by the cyclic ferrocene boronate ester, with complete delocalization, producing a stable ion that is resistant to further fragmentation. This ion represents the residual fragment from the carbohydrate after all other possible carbon atom losses. The initial loss for every O-methyl glycoside is water, to form m/z 370. The propensity to form this ion is dwarfed in comparison to the intensity of the cross pyranose ring fragment at –90 mass units (mu), m/z 298. The m/z 298 ion corresponds to the loss of three carbon atoms from the ring as formaldehyde neutral fragments (–3×CHOH). Related fragments also observed derive from individual carbon losses, –60 mu (m/z 328) and from loss of all of the carbohydrate except the cyclic ferrocenyl boronate ester ring (m/z 254). The early loss of methanol, –32 mu, to form m/z 356, prevails in all diastereomers. The α/β anomeric pair, from O-methyl-D-galactose, is unusual since cross ring assistance from the β anomer's axial C4 hydroxyl controls fragmentation resulting almost exclusively in the MeOH fragment loss. In the α anomer, intensities of fragment ions produced from loss of MeOH are comparable to those seen in any of the other diastereomers. The m/z 314 ion, on the other hand, predominates in the α anomer product ion spectrum, unlike any of the other diastiereomeric products. Those other products that include C 4, 5, 6 and attached OH groups, presumably derive from the loss of two carbon atoms by cross pyranose ring fission.

The distinctive fragment patterns make the pairs easy to distinguish. The galactose pair is even more easily distinguished. However, with no prior knowledge, the glucose and mannose pairs would be quite difficult to identify based on $MS^2$ data. We found that this problem is often resolved by utilizing a $MS^3$ experiment that produces an additional set of fingerprint ions.

Figure 21:
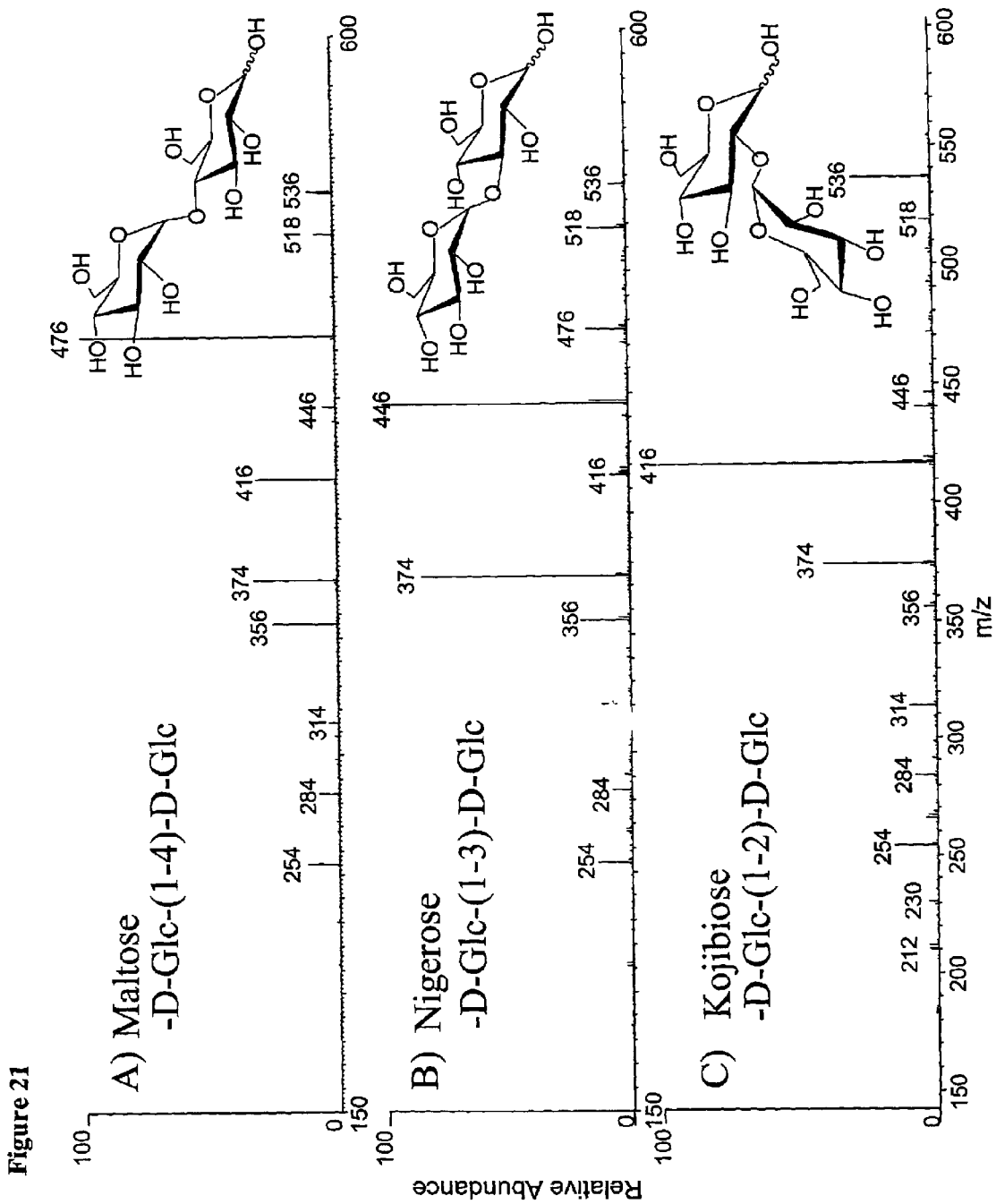
FIG. 21 is a schematic diagram showing the ferrocenyl boronate derivatization of three D-Glc disaccharides: A) Maltose, B) Nigerose, and C) Kojibiose. The linkage positions are 14, 1–3, and 1–2 respectively for each of these three α-linked disaccharides. Linkage position is defined by –60 mu, –90 mu, and –120 mu fragment losses.
Figure 22:
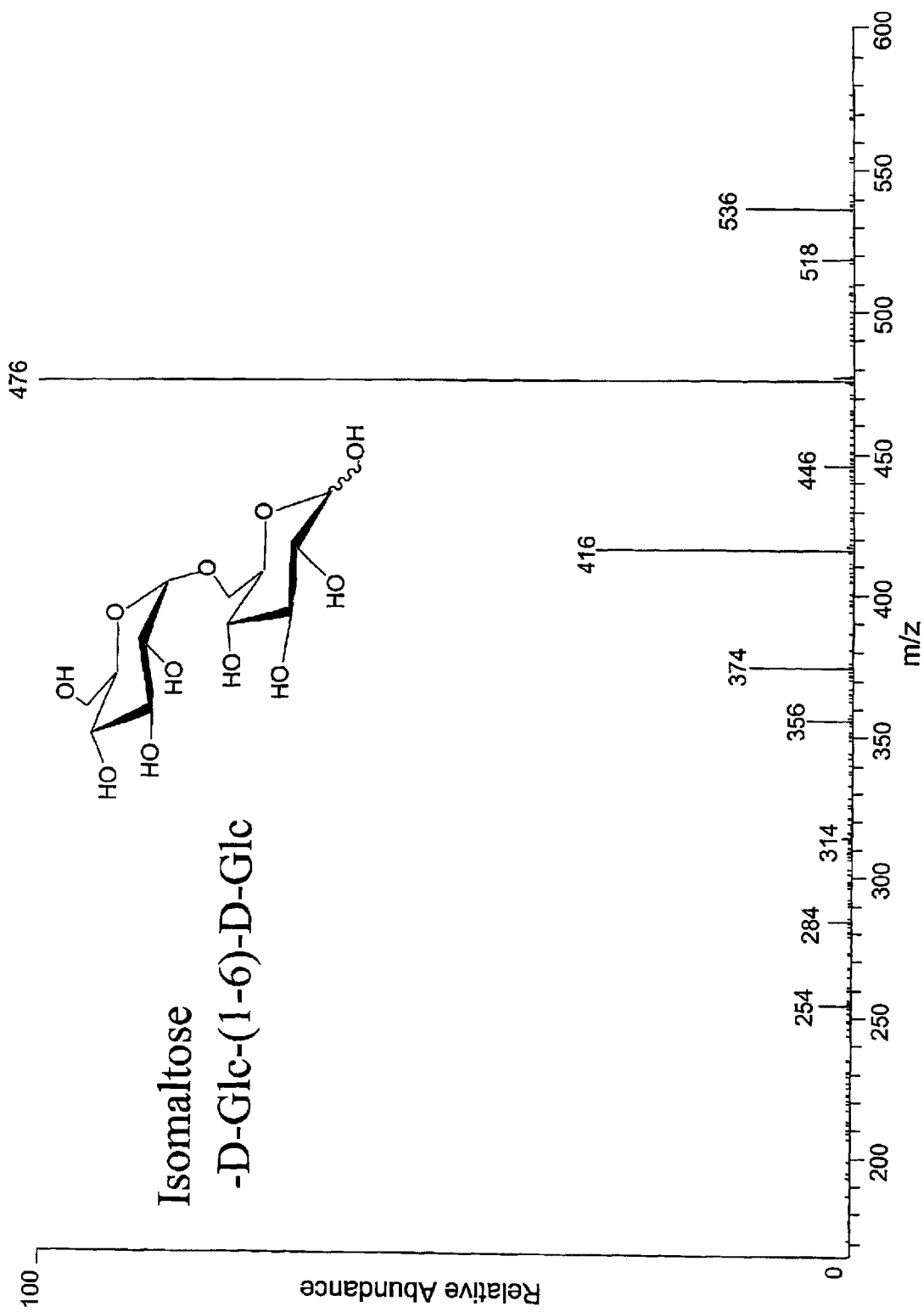
FIG. 22 is a schematic diagram showing a $MS^2$ experiment displays the fingerprint ion set for the β 1–6 linked disaccharide isomaltose. $MS^2$ experiments do not clearly distinguished isomaltose from maltose.
Figure 23:
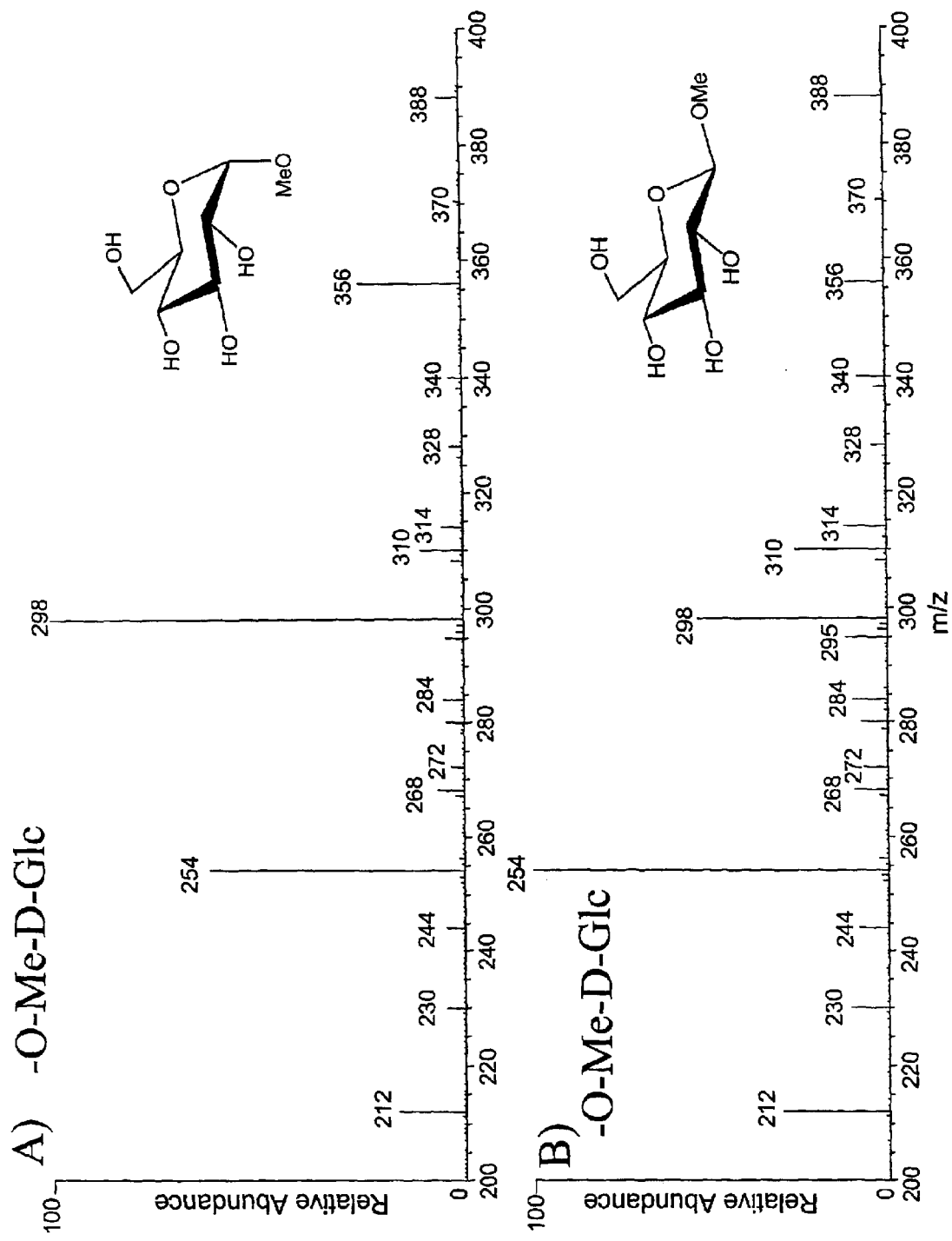
FIG. 23 is a schematic diagram showing the 1–6 and 1–4 α linked D-Glc disaccharides are not clearly distinguishable from the $MS^2$ experiment ion profiles. However, selection of the m/z 356 ion followed by a $MS^3$ experiment results in a distinct ion fingerprint for each.
Figure 24:
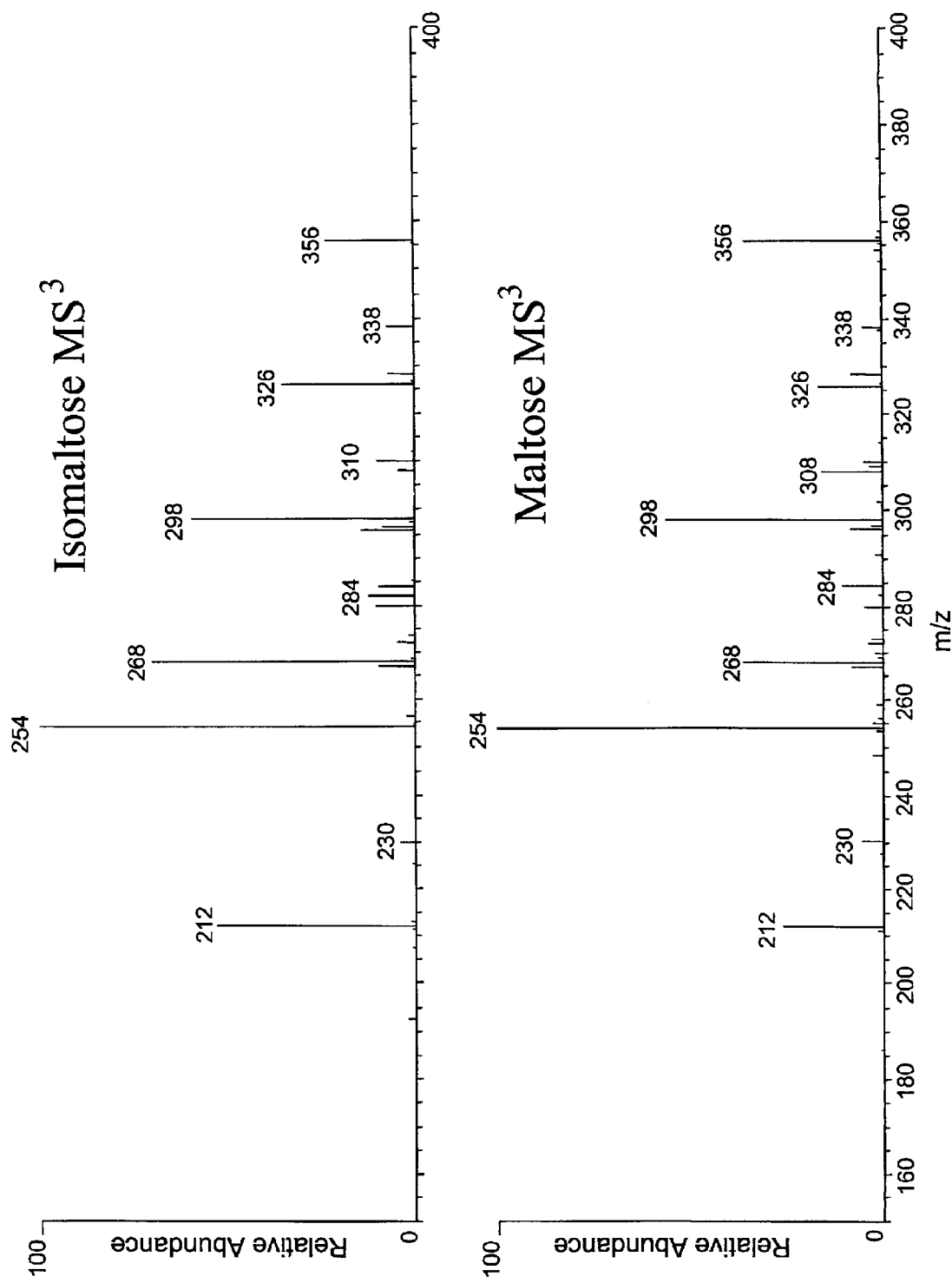
FIG. 24 is a schematic diagram showing $MS^2$ of isomaltose and maltose.

Derivatization as previously described produces a selectable molecular ion at m/z 536. Four diastereomeric disaccharides consisting of D-Glc pairs α linked: 1–2 (Kojibiose), 1–3 (Nigerose), 1–4 (Maltose), and 1–6 (Isomaltose), were selected for analysis. FIG. 21 shows the $MS^2$ spectra at the same approximate concentration and collisional energy for the first three listed compounds. Distinction of the linkage position is clear, in (1–4) a 60 mu loss, m/z 476 predominates. For the (1–3) case, –90 mu, m/z 446 predominates. Finally for the (1–2) case, –120 mu, m/z 416 predominates. Each disaccharide produces a characteristic cross pyranose ring cleavage fragment ion spectrum distinctive in terms of the ion intensity produced, since each cleavage involves a two-bond rupture. The 1–6 linkage of isomaltose (FIG. 22) is not so clear cut. The predominant fragment loss of two carbons to produce m/z 476 as the principal ion is quite similar to maltose. Further CID selection of the fragment that represents the bifurcation of the disaccharide, m/z 356, in an $MS^3$ experiment, yields two spectra that are notably different. When a series of O-methyl glycosides and a suite of related D-Glc disaccharides were derivatized by dilution-mixing they produced distinctive derivative ions that were selected in either $MS^2$ or $MS^3$ experiments. The spectra produced by fragmenting an isobaric population of molecular ions formed by single electron oxidation of the derivative in the spray device provides a fingerprinting method for very closely related species.

EXAMPLE 4

Figure 25:
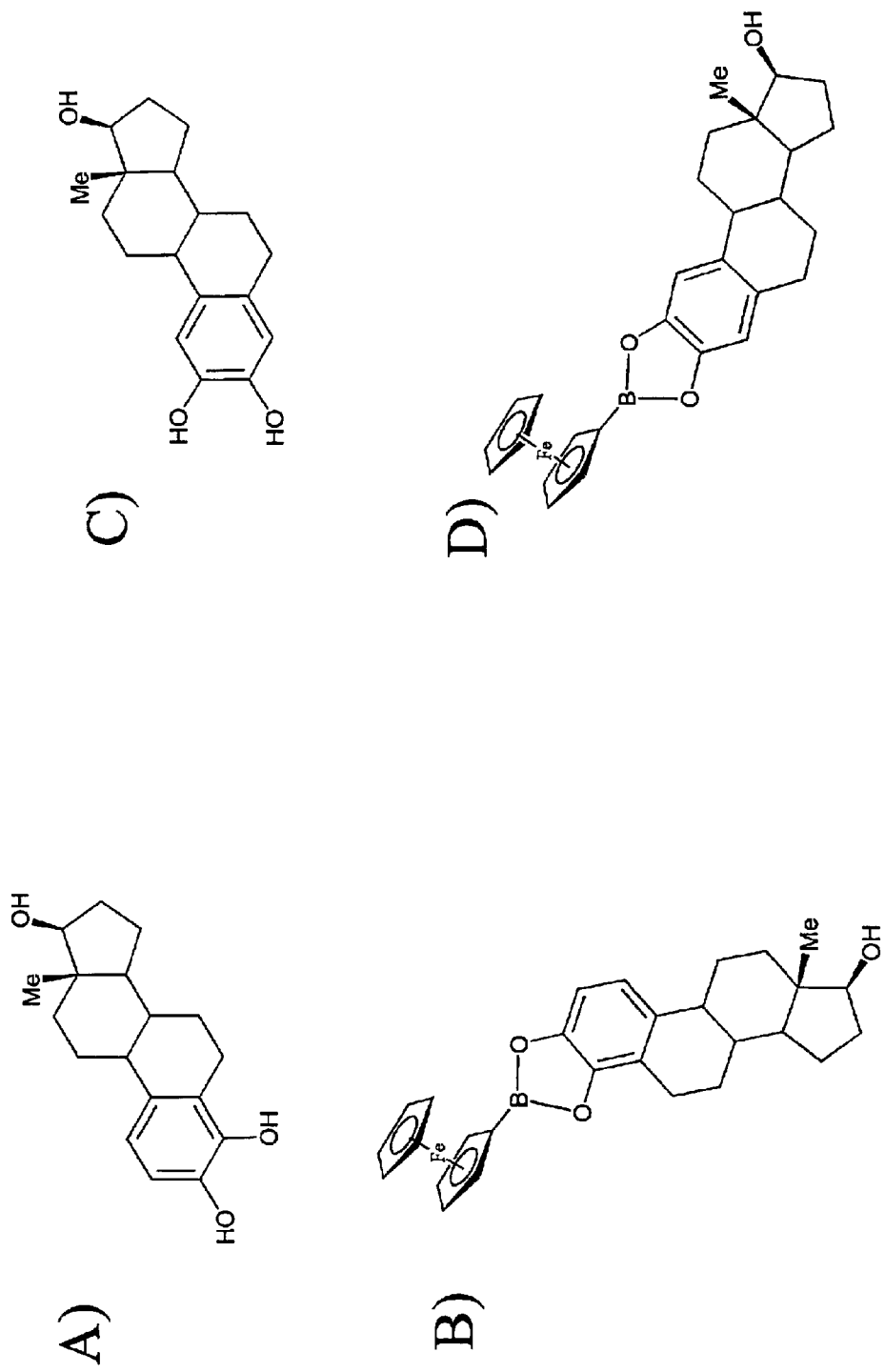
FIG. 25 is a schematic diagram showing the structures of catechol estrogens and their ferrocenyl boronic ester complexes: A) 4-Hydroxyestradiol; B) Ferrocenyl boronic ester of 4-Hydroxyestradiol; C) 2-Hydroxyestradiol and D) Ferrocenyl boronic ester of 2-Hydroxyestradiol.
Figure 26:
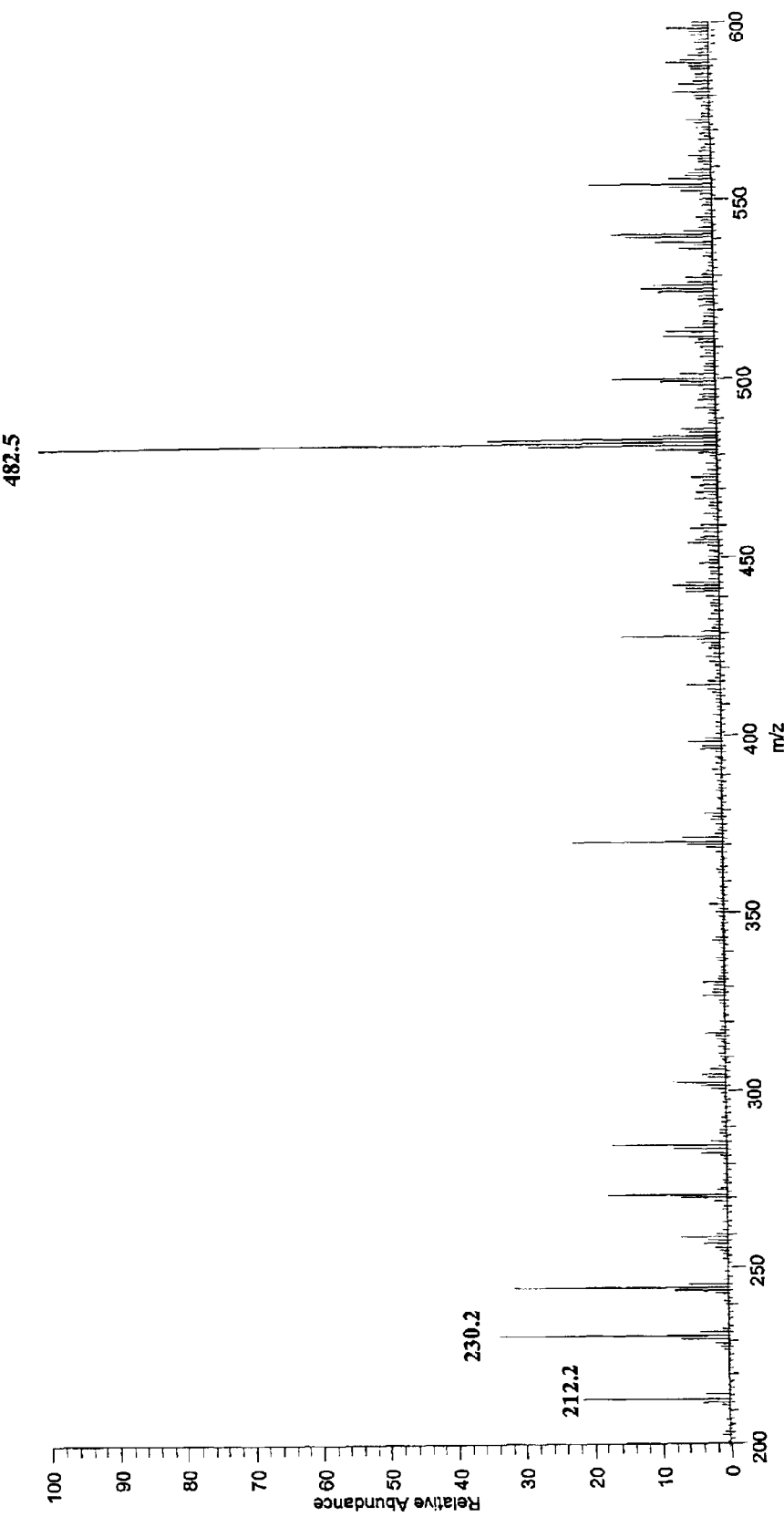
FIG. 26 is a schematic diagram showing the fill scan ES-MS of 2 or 4-Hydroxyestradiol ferrocenyl boronate complex including a radical cation at 482 Da.
Figure 27:
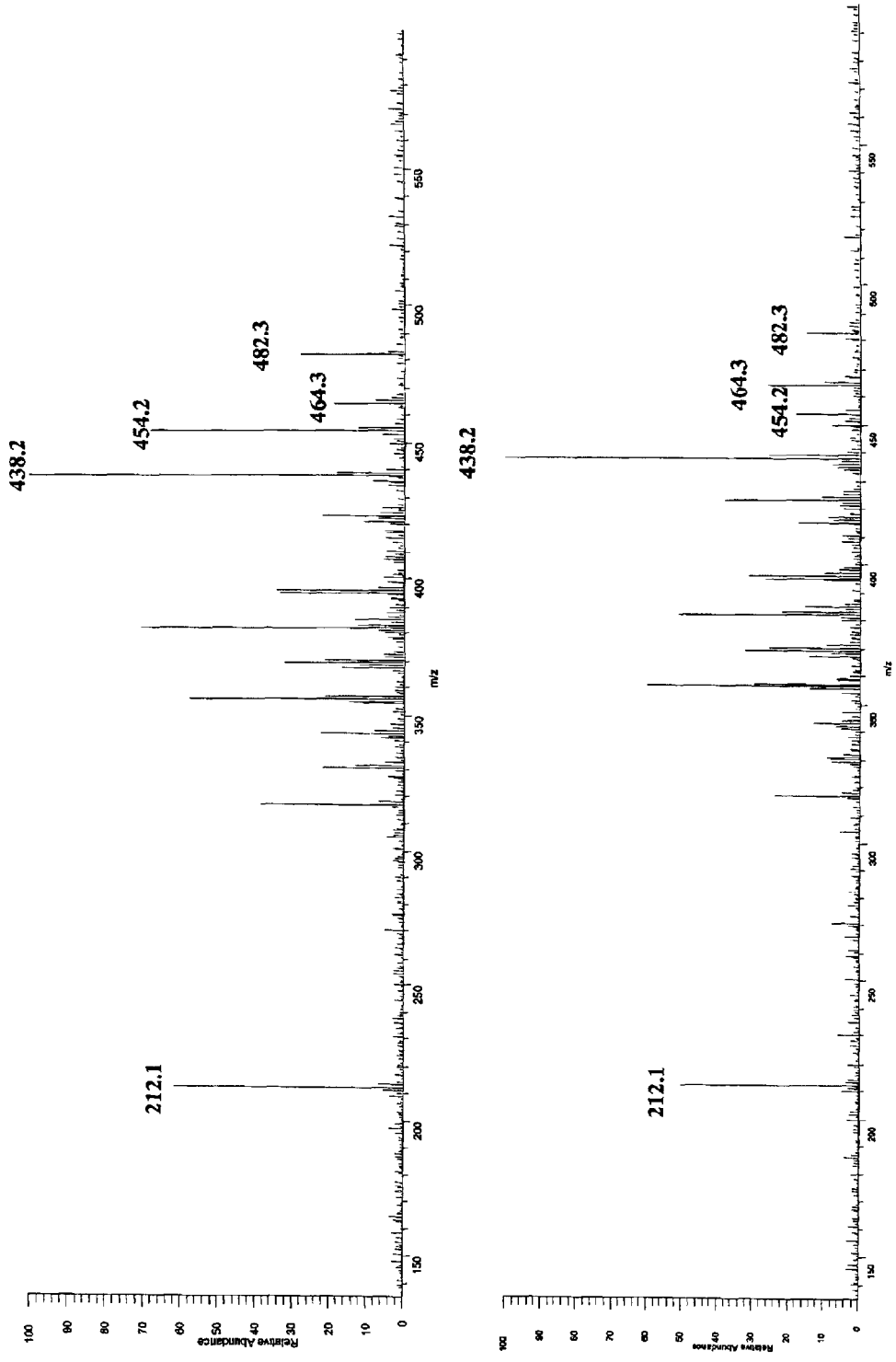
FIG. 27 is a schematic diagram showing the $MS^2$ fragmentation spectra of 482 Da selected ion 2-Hydroxyestradiol ferrocene boronate and 4-Hydroxyestradiol ferrocene boronate.
Figure 28:
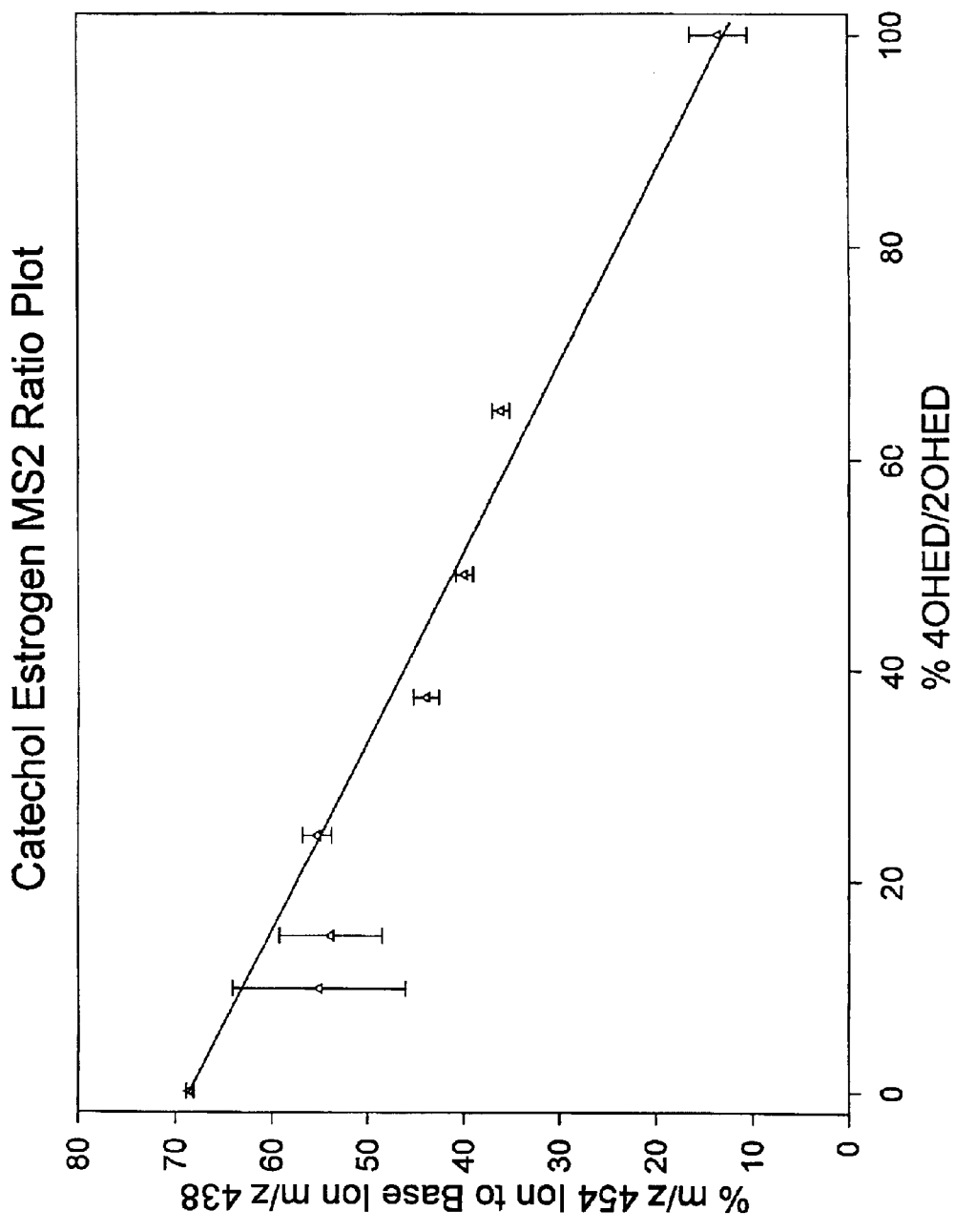
FIG. 28 is a schematic diagram showing the catechol estrogen $MS^2$ Ratio Plot.

Both 2- and 4-OHE exhibit a geminal diol functionality that may be exploited by converting these electrospray neutral molecules into ferrocene boronate complexes (FIG. 25) that are readily amenable to tandem ES-MS analysis. The ferrocene boronic acid derivatizing agent produces a suite of ions with the principle peak at m/z 230.2 (FIG. 27). The natural abundance of iron and boron isotopes creates a complex pattern of ions for all species containing these elements. Infusion of either 2-OHE or 4-OHE ferrocene boronate esters produces a peak at m/z 482.4 corresponding to the molecular ion. Selection and collision induced dissociation (CID) of that ion in the trap produces a rich fragment ion spectrum (FIG. 27). The CID spectra for the two isomers are very similar with a base peak at m/z 438. However, the fragment at m/z 454, which is likely derived from the neutral loss of ethylene from the "C" ring is much more intense for the 4-OHE isomer (74 vs 17%). Spraying mixtures of the two isomer standards yields data for a plot of the mole ratio of the isomers as a function of the intensity of the m/z 454.3 ion measured as a percentage of base peak (m/z 438.3) (FIG. 28). In this way the signal strength of this ion may be used to estimate the isomeric composition of any mixture. The limits of detection for this method indicate that the single-electron ferrocenyl boronate esters are detectable at the nM level, which is an advantage for biologically derived analyses.

Although specific embodiments of the invention are herein disclosed for purposes of explanation, various modifications thereof, after study of this specification, will be apparent to those skilled in the art to which the invention pertains.

What is claimed is:

1. In an analytical method for characterizing the structure of a catechol estrogen by electrospray tandem mass spectrometry, the improvement which comprises derivatizing the catechol estrogen with ferrocenyl boronate.

2. The improvement of claim 1, wherein the catechol estrogen is 2-hydroxyestradiol.

3. The improvement of claim 1, wherein the catechol estrogen is 4-hydroxyestradiol.

* * * * *